US008070749B2

(12) United States Patent
Stern

(10) Patent No.: US 8,070,749 B2
(45) Date of Patent: Dec. 6, 2011

(54) REVISABLE ANTERIOR CERVICAL PLATING SYSTEM

(76) Inventor: Joseph D. Stern, Greensboro, NC (US)

( * ) Notice: Subject to any disclaimer, the term of this patent is extended or adjusted under 35 U.S.C. 154(b) by 710 days.

(21) Appl. No.: 11/453,440

(22) Filed: Jun. 14, 2006

(65) Prior Publication Data

US 2006/0276794 A1 Dec. 7, 2006

Related U.S. Application Data

(63) Continuation-in-part of application No. 11/417,794, filed on May 3, 2006.

(60) Provisional application No. 60/680,728, filed on May 12, 2005.

(51) Int. Cl.
*A61B 17/56* (2006.01)
*A61B 17/58* (2006.01)
*A61B 17/80* (2006.01)
*A61F 2/30* (2006.01)

(52) U.S. Cl. ....................................................... 606/71

(58) Field of Classification Search .................. 606/295, 606/296, 70, 71, 280, 282, 283, 287; 411/372.5, 411/373, 374, 383
See application file for complete search history.

(56) References Cited

U.S. PATENT DOCUMENTS

| 4,243,025 | A |   | 1/1981  | Jones             |        |
|-----------|---|---|---------|-------------------|--------|
| 5,180,381 | A |   | 1/1993  | Aust et al.       |        |
| 5,364,399 | A |   | 11/1994 | Lowery et al.     |        |
| 5,520,690 | A |   | 5/1996  | Errico et al.     |        |
| 5,531,746 | A |   | 7/1996  | Errico et al.     |        |
| 5,558,674 | A |   | 9/1996  | Heggeness et al.  |        |
| 5,603,713 | A |   | 2/1997  | Aust et al.       |        |
| 5,607,426 | A |   | 3/1997  | Ralph et al.      |        |
| 5,616,142 | A | * | 4/1997  | Yuan et al.       | 606/71 |
| 5,643,265 | A |   | 7/1997  | Errico et al.     |        |
| 5,676,703 | A |   | 10/1997 | Gelbard           |        |
| 5,766,254 | A |   | 6/1998  | Gelbard           |        |
| 5,888,221 | A |   | 3/1999  | Gelbard           |        |
| 5,904,683 | A |   | 5/1999  | Pohndorf et al.   |        |
| 5,954,722 | A |   | 9/1999  | Bono              |        |
| 5,989,250 | A |   | 11/1999 | Wagner et al.     |        |
| 6,017,345 | A |   | 1/2000  | Richelsoph        |        |
| 6,030,389 | A |   | 2/2000  | Wagner et al.     |        |
| 6,080,193 | A |   | 6/2000  | Hochshuler et al. |        |
| 6,139,550 | A |   | 10/2000 | Michelson         |        |
| 6,152,927 | A |   | 11/2000 | Farris et al.     |        |
| 6,159,213 | A |   | 12/2000 | Rogozinski        |        |
| 6,193,721 | B1|   | 2/2001  | Michelson         |        |
| D440,311  | S |   | 4/2001  | Michelson         |        |

(Continued)

OTHER PUBLICATIONS

International Search Report for International Application No. PCT/us2006/016821, filed May 3, 2006, Search Report completed May 4, 2007, mailed Aug. 13, 2007, 3 pgs.

(Continued)

*Primary Examiner* — Thomas Barrett
*Assistant Examiner* — David Bates
(74) *Attorney, Agent, or Firm* — Kauth, Pomeroy, Peck & Bailey LLP

(57) ABSTRACT

An improved anterior cervical plating system and methods of cervical fusion using such a system are provided. The cervical plating system includes an interlocking mechanism that integrated into each of the plates such that any two plates may cooperatively engage through the interlocking mechanism such that a new cervical plate can be interconnected with a pre-existing plate during revision surgery without removal of the pre-existing plate.

34 Claims, 43 Drawing Sheets

U.S. PATENT DOCUMENTS

| | | | |
|---|---|---|---|
| 6,224,602 B1 | 5/2001 | Hayes | |
| 6,231,610 B1 | 5/2001 | Geisler | |
| 6,235,034 B1 | 5/2001 | Bray | |
| 6,258,089 B1 | 7/2001 | Campbell et al. | |
| 6,273,889 B1 | 8/2001 | Richelsoph | |
| 6,293,949 B1 | 9/2001 | Justis et al. | |
| D449,692 S | 10/2001 | Michelson | |
| 6,306,136 B1 | 10/2001 | Baccelli | |
| 6,331,179 B1 | 12/2001 | Freid et al. | |
| 6,340,362 B1 * | 1/2002 | Pierer et al. | 606/71 |
| 6,342,074 B1 | 1/2002 | Simpson | |
| 6,383,186 B1 | 5/2002 | Michelson | |
| 6,398,783 B1 * | 6/2002 | Michelson | 606/70 |
| 6,402,756 B1 | 6/2002 | Ralph et al. | |
| 6,416,515 B1 | 7/2002 | Wagner | |
| 6,416,528 B1 | 7/2002 | Michelson | |
| 6,428,542 B1 | 8/2002 | Michelson | |
| 6,440,444 B2 | 8/2002 | Boyce et al. | |
| 6,454,769 B2 | 9/2002 | Wagner et al. | |
| 6,454,771 B1 | 9/2002 | Michelson | |
| 6,503,250 B2 | 1/2003 | Paul | |
| 6,506,191 B1 * | 1/2003 | Joos | 606/86 B |
| 6,533,786 B1 | 3/2003 | Needham et al. | |
| 6,562,040 B1 | 5/2003 | Wagner | |
| 6,576,016 B1 | 6/2003 | Hochshuler et al. | |
| 6,592,586 B1 | 7/2003 | Michelson | |
| 6,595,992 B1 | 7/2003 | Wagner et al. | |
| 6,599,290 B2 | 7/2003 | Bailey et al. | |
| 6,602,256 B1 * | 8/2003 | Hayes | 606/296 |
| 6,613,050 B1 | 9/2003 | Wagner et al. | |
| 6,613,053 B1 | 9/2003 | Collins et al. | |
| 6,620,163 B1 | 9/2003 | Michelson | |
| 6,626,907 B2 | 9/2003 | Campbell et al. | |
| 6,641,614 B1 | 11/2003 | Wagner et al. | |
| 6,645,208 B2 | 11/2003 | Apfelbaum et al. | |
| 6,652,525 B1 | 11/2003 | Assaker et al. | |
| 6,666,867 B2 | 12/2003 | Ralph et al. | |
| 6,669,699 B2 | 12/2003 | Ralph et al. | |
| 6,669,700 B1 | 12/2003 | Farris et al. | |
| 6,679,883 B2 | 1/2004 | Hawkes et al. | |
| 6,689,134 B2 | 2/2004 | Ralph et al. | |
| 6,692,503 B2 | 2/2004 | Foley et al. | |
| 6,695,845 B2 | 2/2004 | Dixon et al. | |
| 6,695,846 B2 | 2/2004 | Richelsoph et al. | |
| 6,761,719 B2 | 7/2004 | Justis et al. | |
| 6,764,489 B2 | 7/2004 | Ferree | |
| 6,770,075 B2 | 8/2004 | Howland | |
| 6,780,186 B2 | 8/2004 | Errico et al. | |
| 6,837,905 B1 | 1/2005 | Lieberman | |
| 6,843,790 B2 | 1/2005 | Ferree | |
| 6,855,147 B2 | 2/2005 | Harrington, Jr. | |
| D505,205 S | 5/2005 | Freid | |
| 6,890,335 B2 | 5/2005 | Grabowski et al. | |
| 6,916,320 B2 | 7/2005 | Michelson | |
| 6,926,718 B1 | 8/2005 | Michelson | |
| 6,932,820 B2 | 8/2005 | Osman | |
| 6,936,050 B2 | 8/2005 | Michelson | |
| 6,936,051 B2 | 8/2005 | Michelson | |
| 6,964,664 B2 | 11/2005 | Freid et al. | |
| 6,969,390 B2 | 11/2005 | Michelson | |
| 6,972,019 B2 | 12/2005 | Michelson | |
| 7,001,387 B2 | 2/2006 | Farris et al. | |
| 7,001,389 B1 | 2/2006 | Navarro et al. | |
| 7,004,944 B2 | 2/2006 | Gause | |
| 7,008,426 B2 | 3/2006 | Paul | |
| 7,008,427 B2 | 3/2006 | Sevrain | |
| 7,025,769 B1 | 4/2006 | Ferree | |
| 7,044,952 B2 | 5/2006 | Michelson | |
| 7,048,739 B2 * | 5/2006 | Konieczynski et al. | 606/288 |
| 7,318,825 B2 * | 1/2008 | Butler et al. | 606/71 |
| 7,341,590 B2 * | 3/2008 | Ferree | 606/915 |
| 7,527,641 B2 * | 5/2009 | Suh | 606/289 |
| 7,615,068 B2 * | 11/2009 | Timm et al. | 606/266 |
| 2003/0036759 A1 | 2/2003 | Musso | |
| 2003/0060828 A1 * | 3/2003 | Michelson | 606/71 |
| 2003/0074001 A1 * | 4/2003 | Apfelbaum et al. | 606/71 |
| 2003/0187509 A1 | 10/2003 | Lemole, Jr. | |
| 2003/0212399 A1 * | 11/2003 | Dinh et al. | 606/61 |
| 2004/0210217 A1 * | 10/2004 | Baynham et al. | 606/61 |
| 2005/0216011 A1 | 9/2005 | Paul | |
| 2006/0116681 A1 | 6/2006 | Bert | |
| 2006/0122607 A1 * | 6/2006 | Kolb | 606/71 |
| 2006/0217715 A1 * | 9/2006 | Serhan et al. | 606/61 |
| 2006/0264946 A1 * | 11/2006 | Young | 606/69 |
| 2007/0093838 A1 * | 4/2007 | Khodadadyan-Klostermann et al. | 606/70 |
| 2008/0234681 A1 * | 9/2008 | Baynham | 606/71 |

OTHER PUBLICATIONS

Written Opinion for International Application No. PCT/US2006/016821, filed May 3, 2006, Search Report completed May 4, 2007, mailed Aug. 13, 2007, 6 pgs.

* cited by examiner

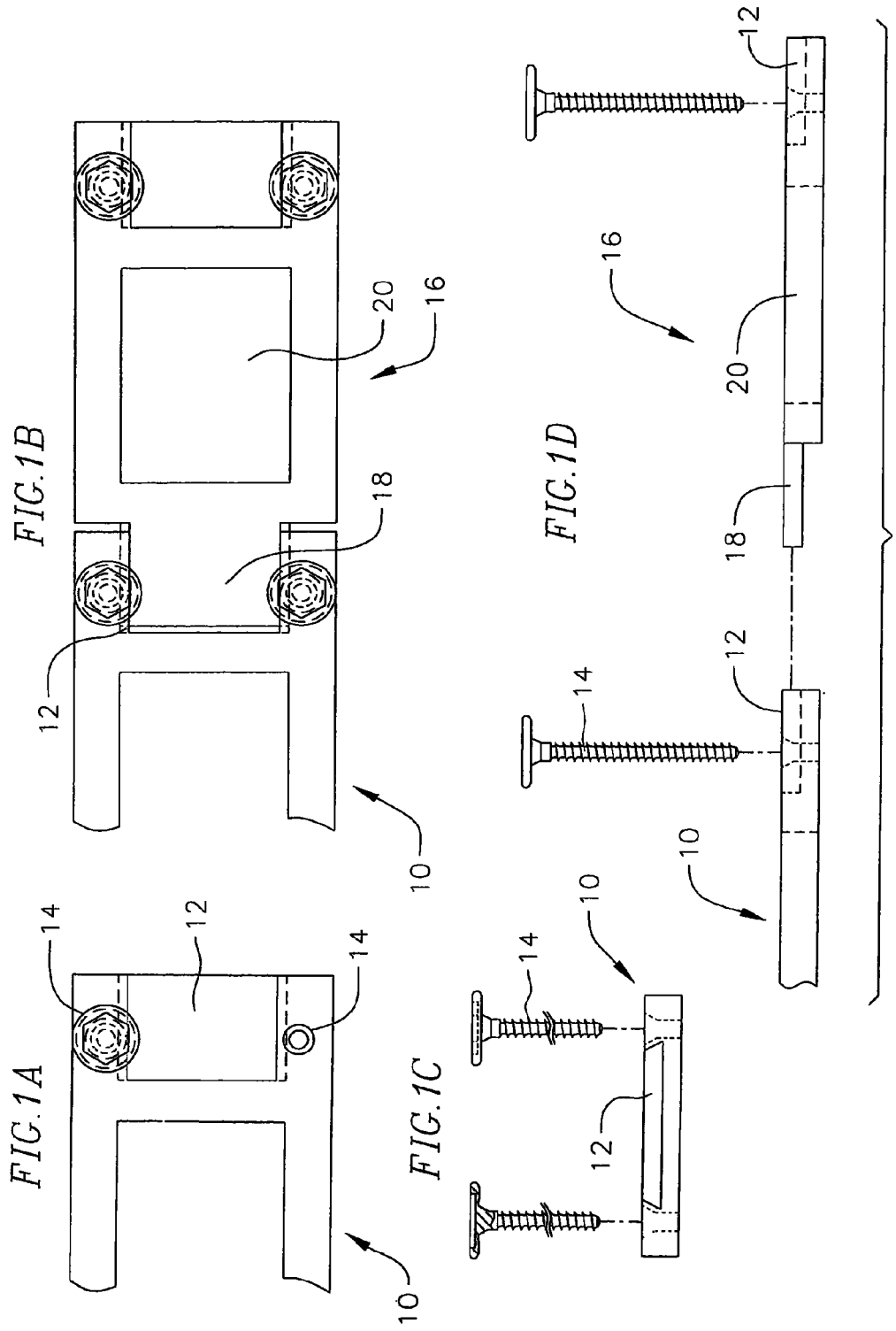

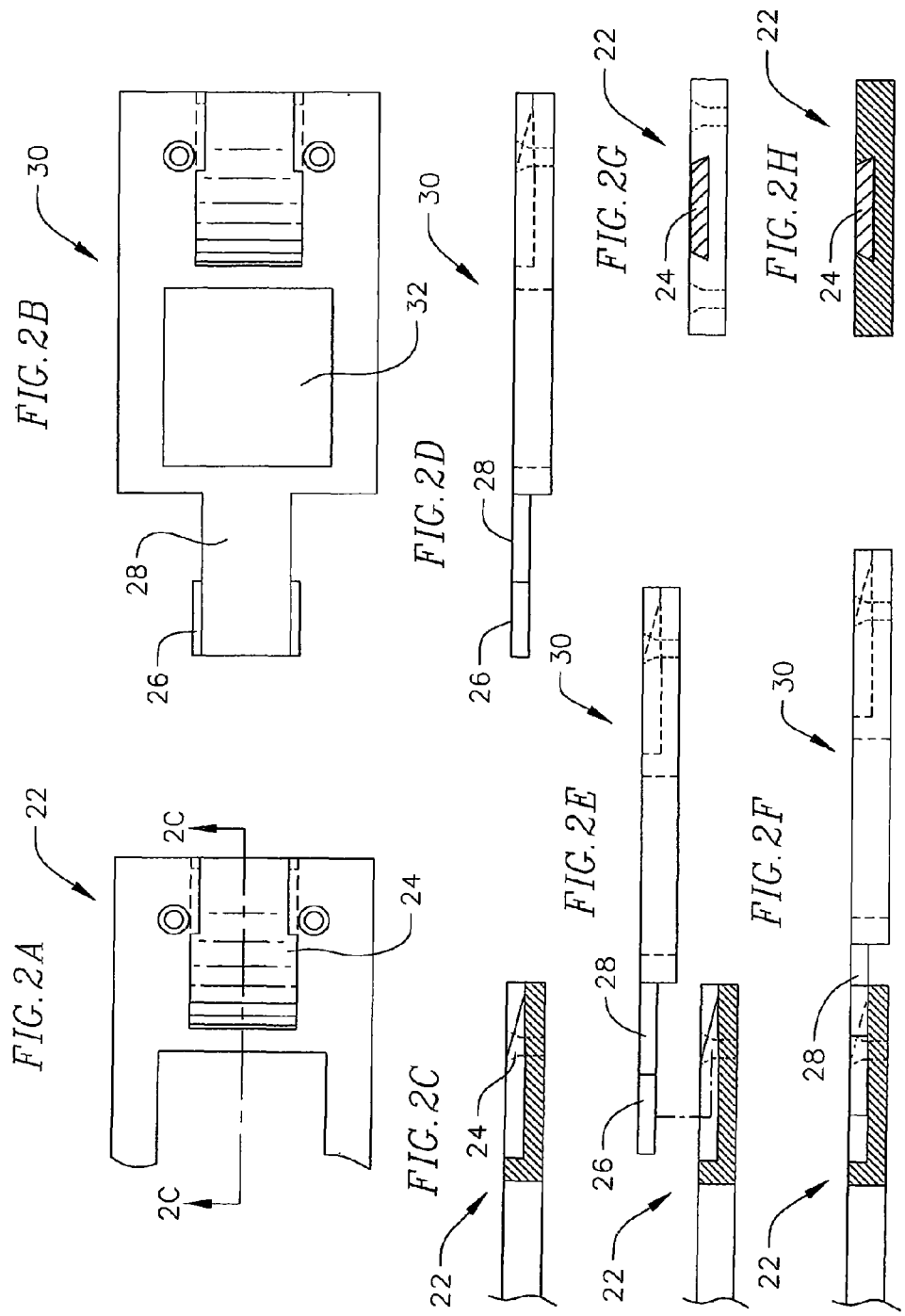

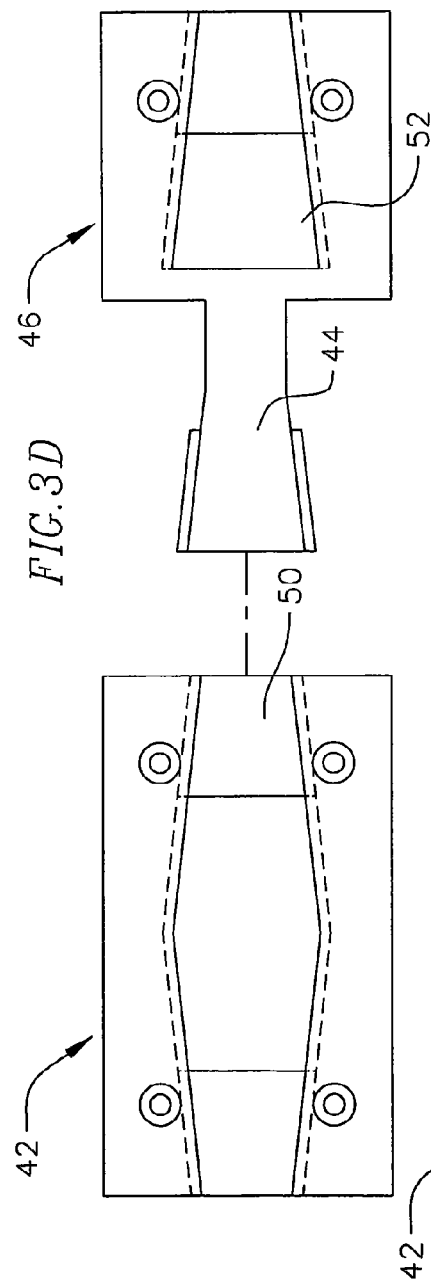
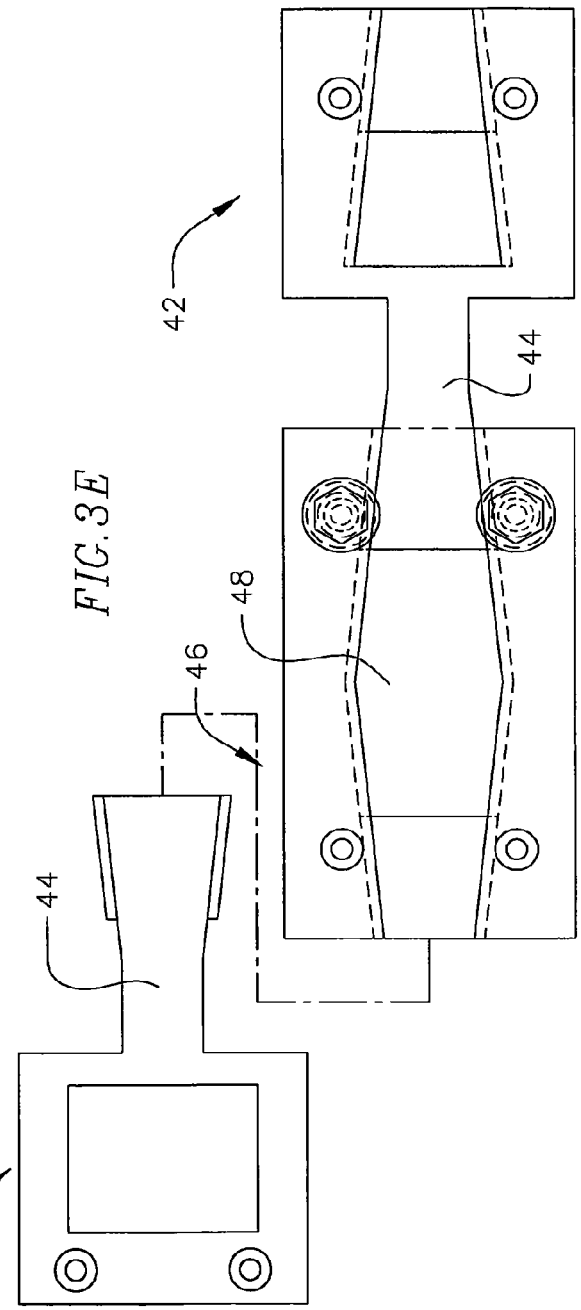

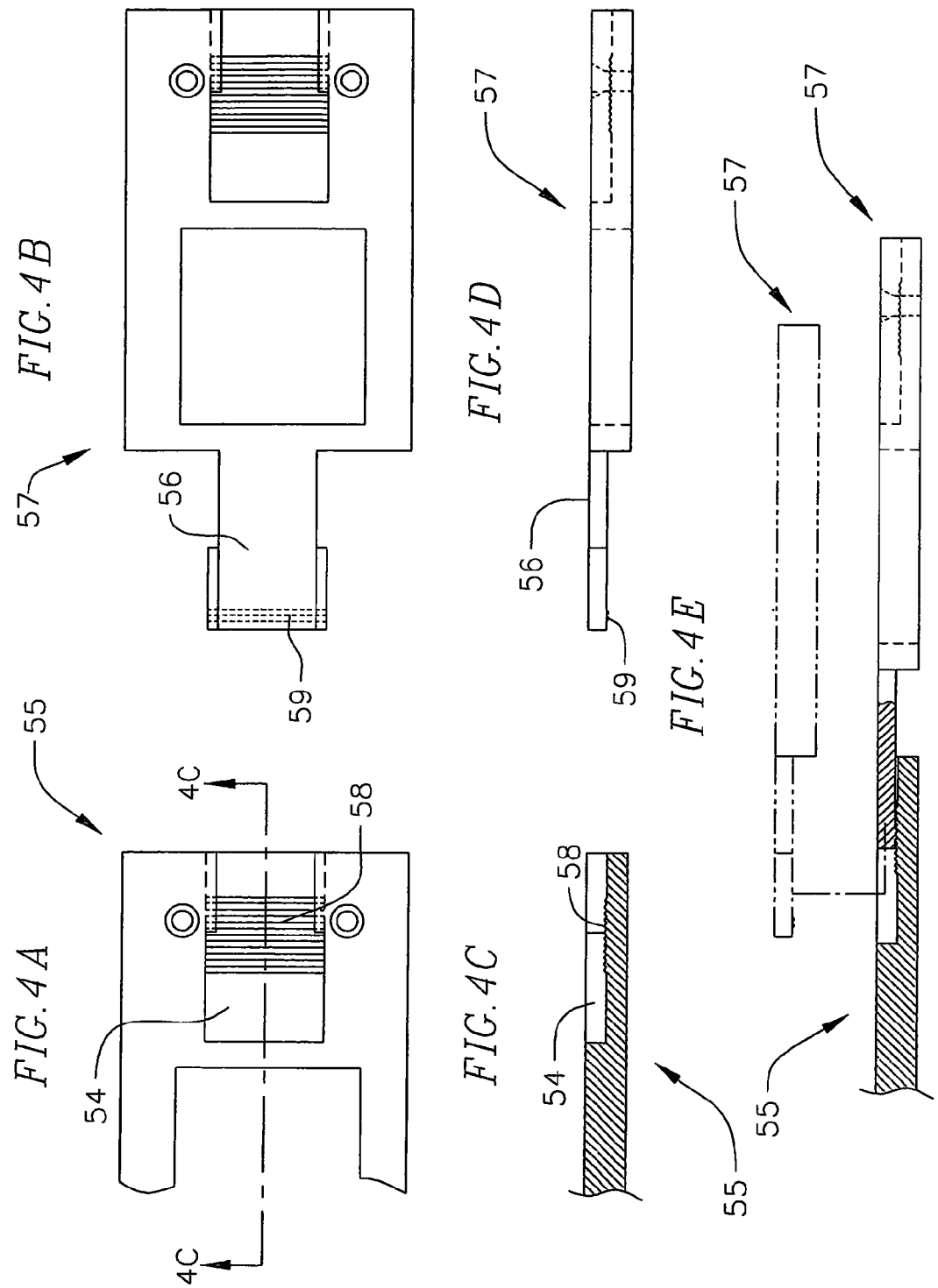

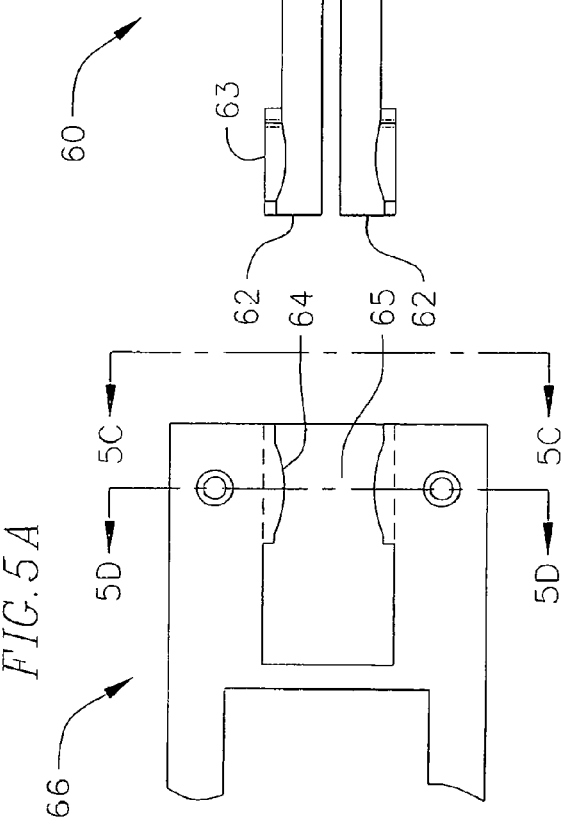
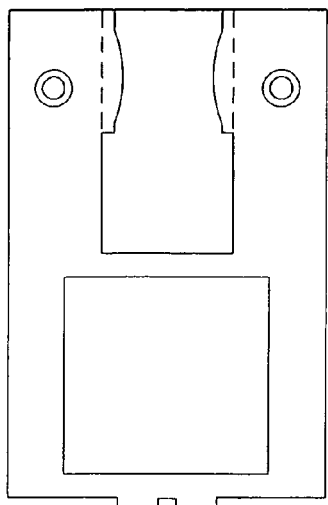
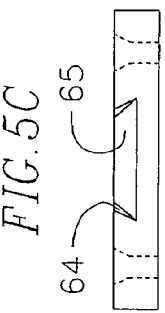
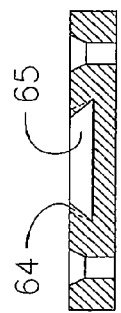

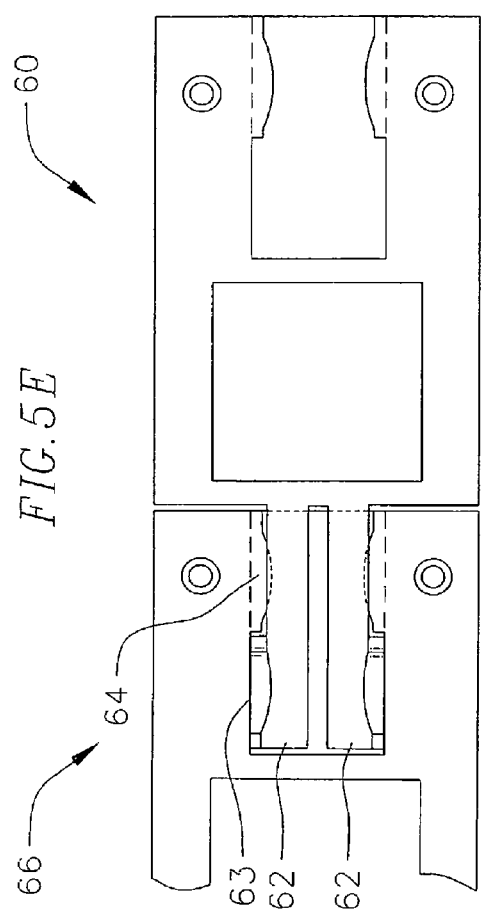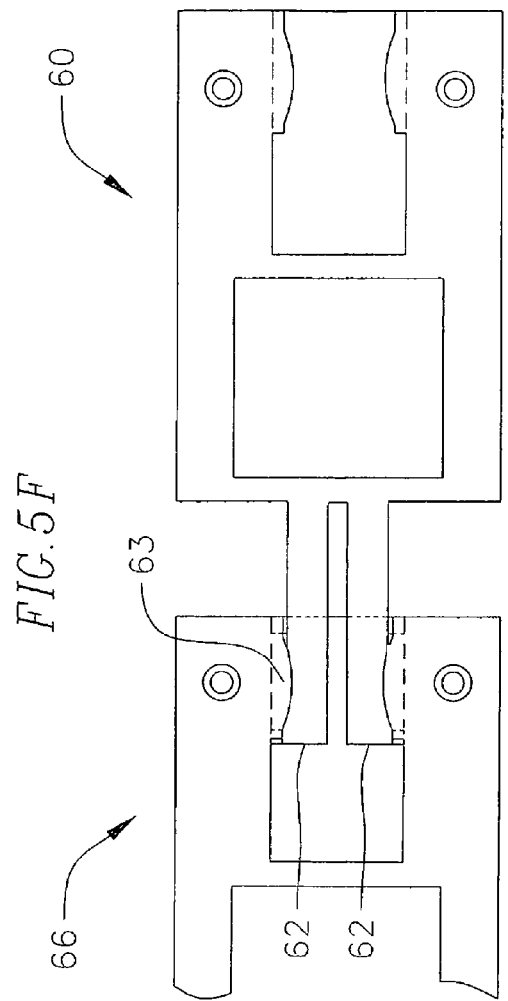

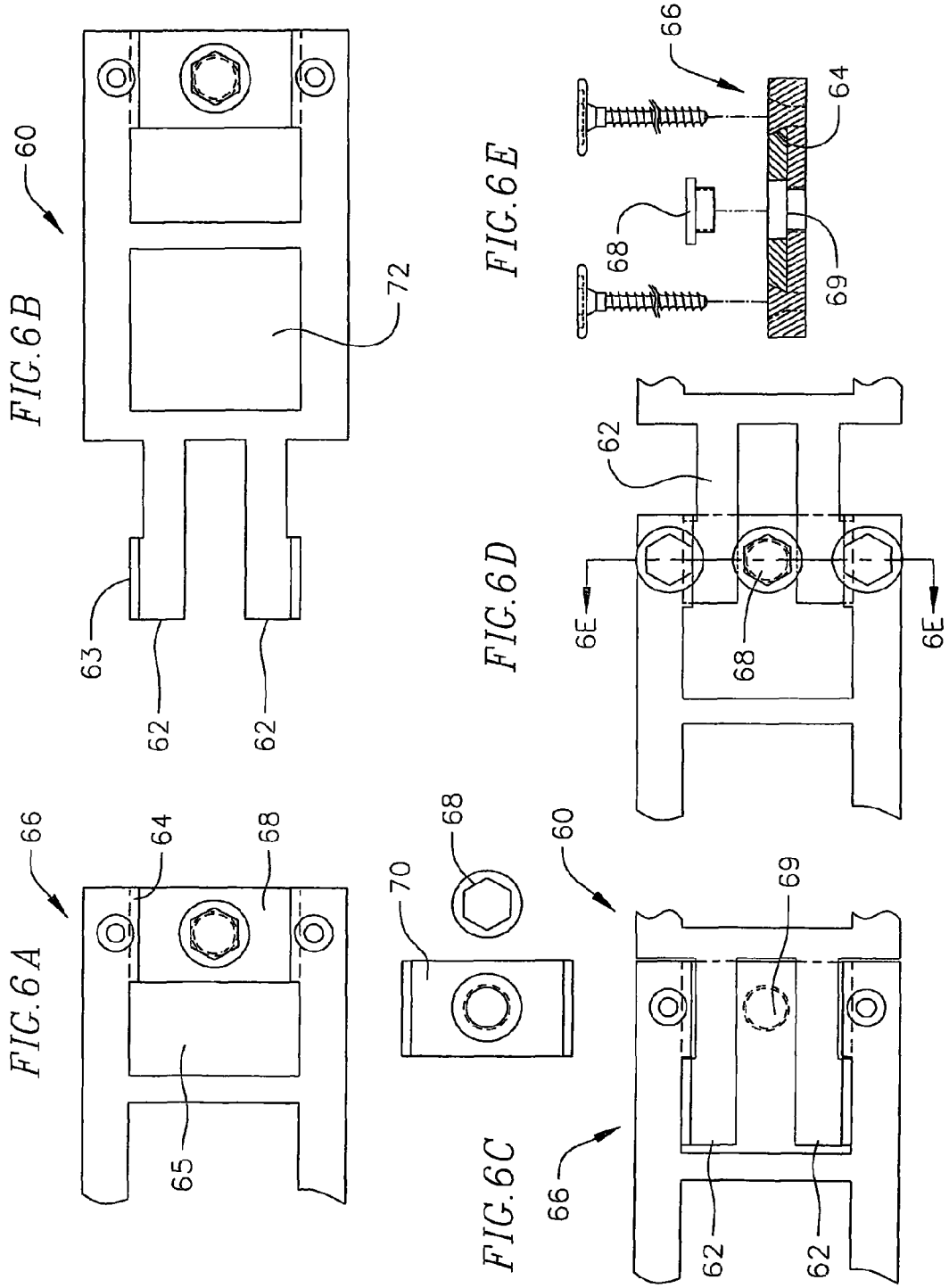

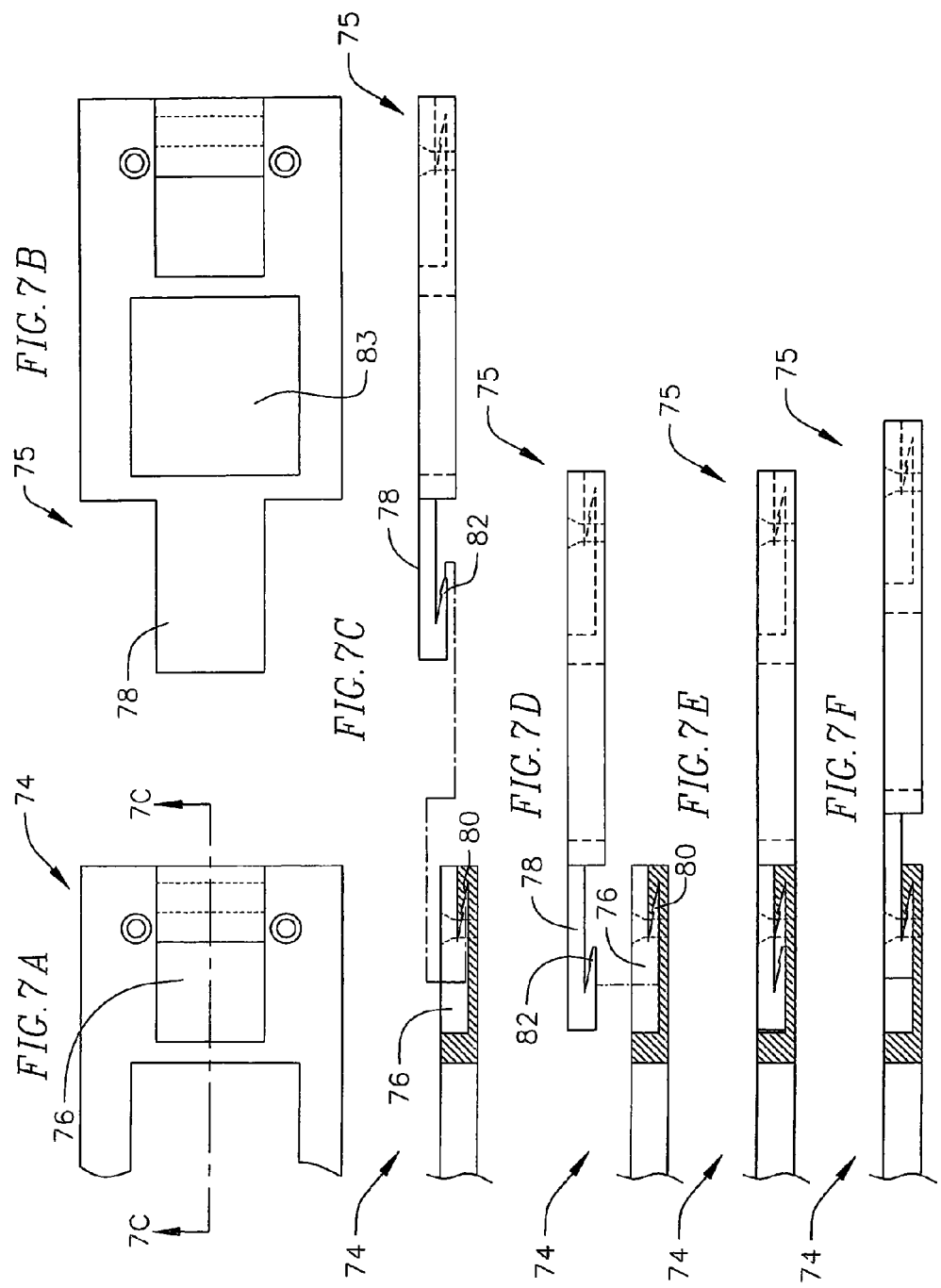

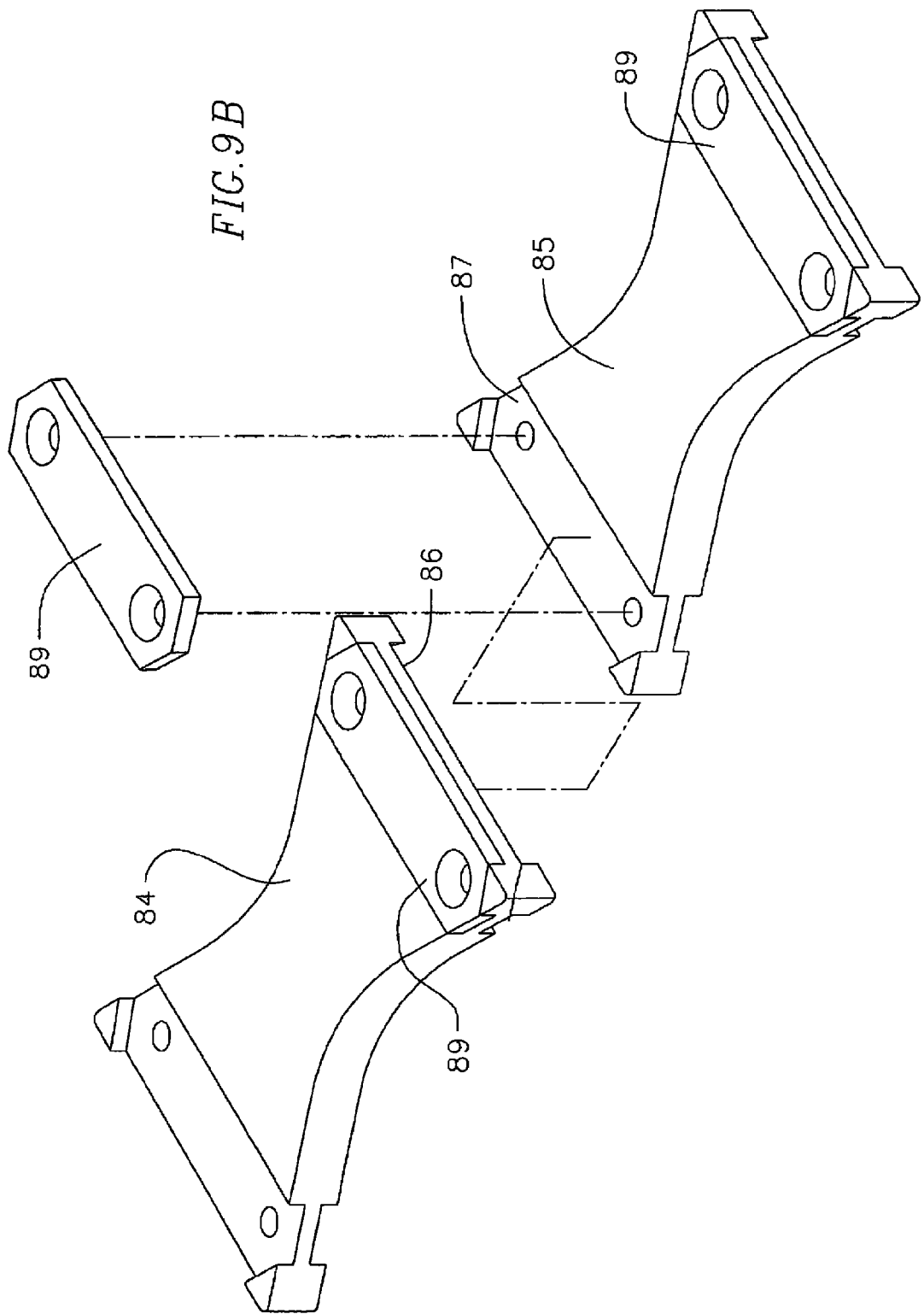

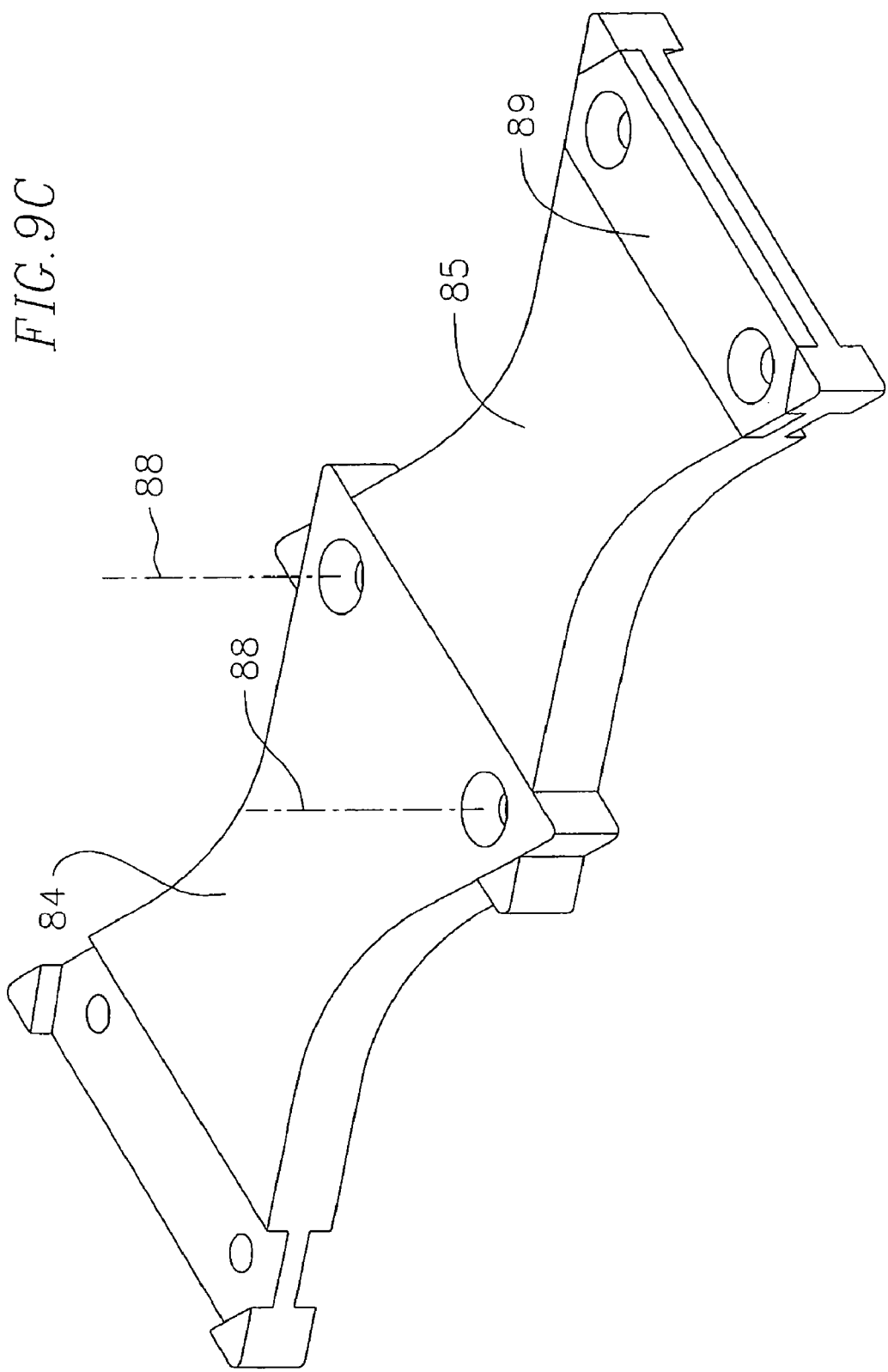

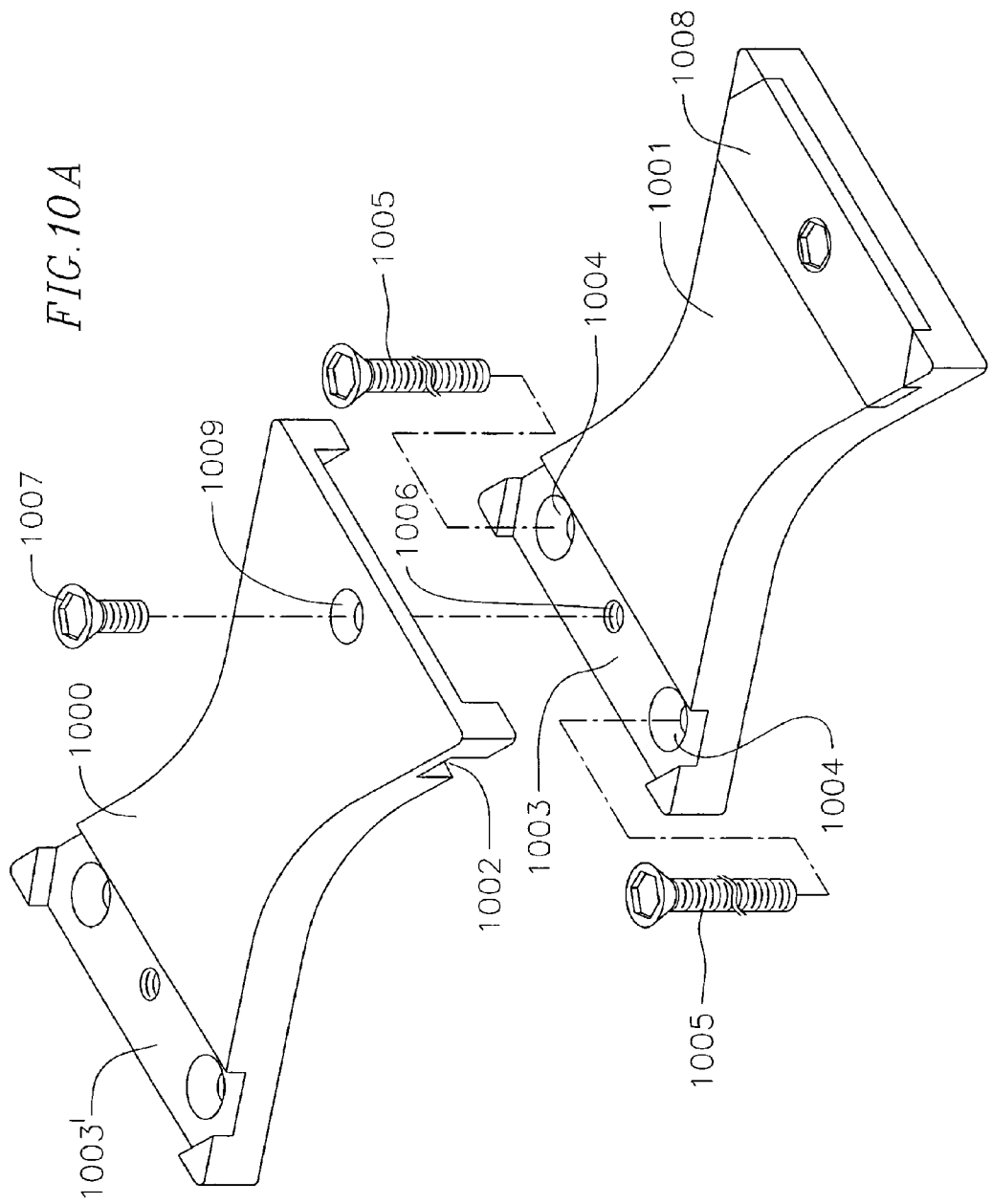

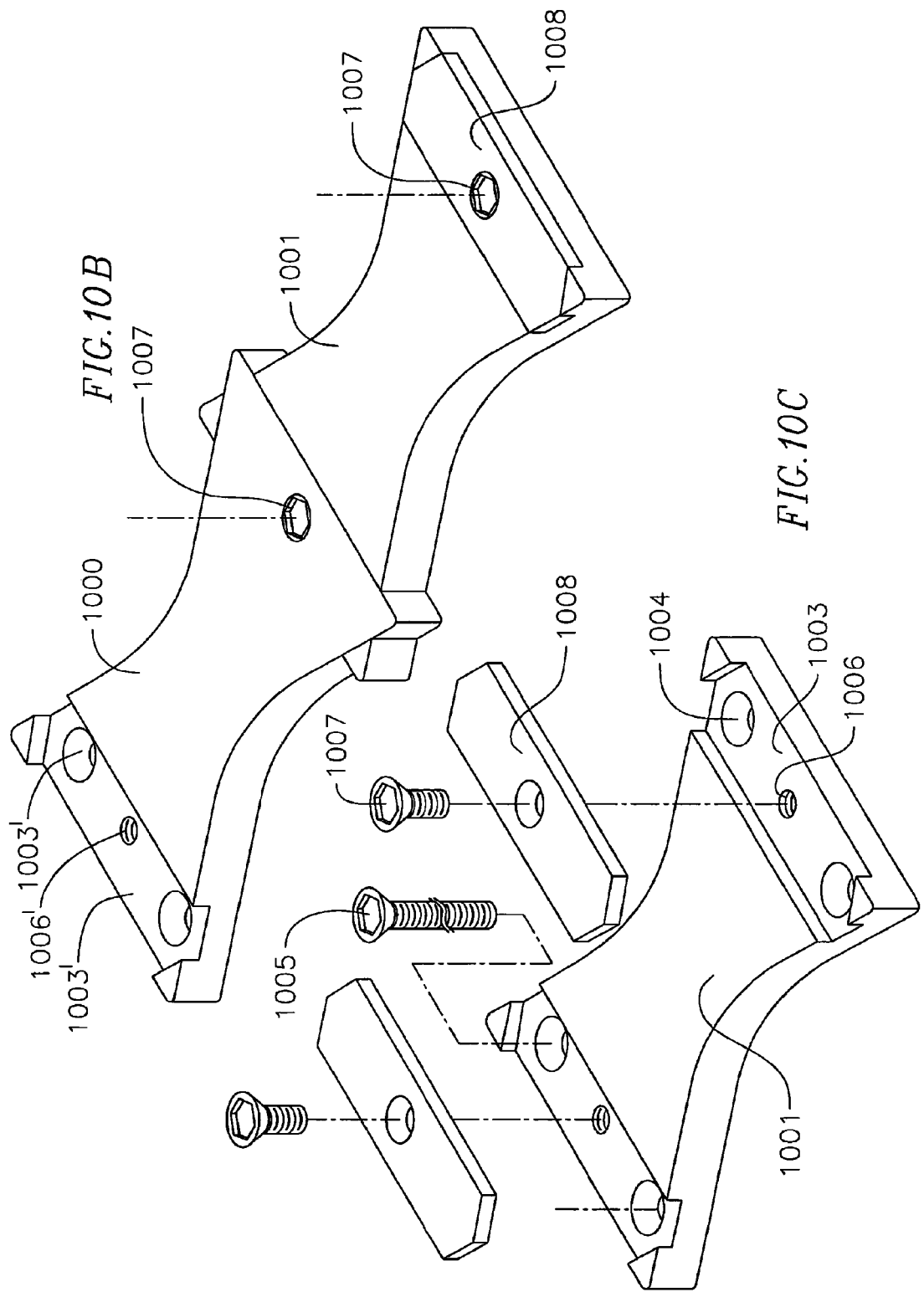

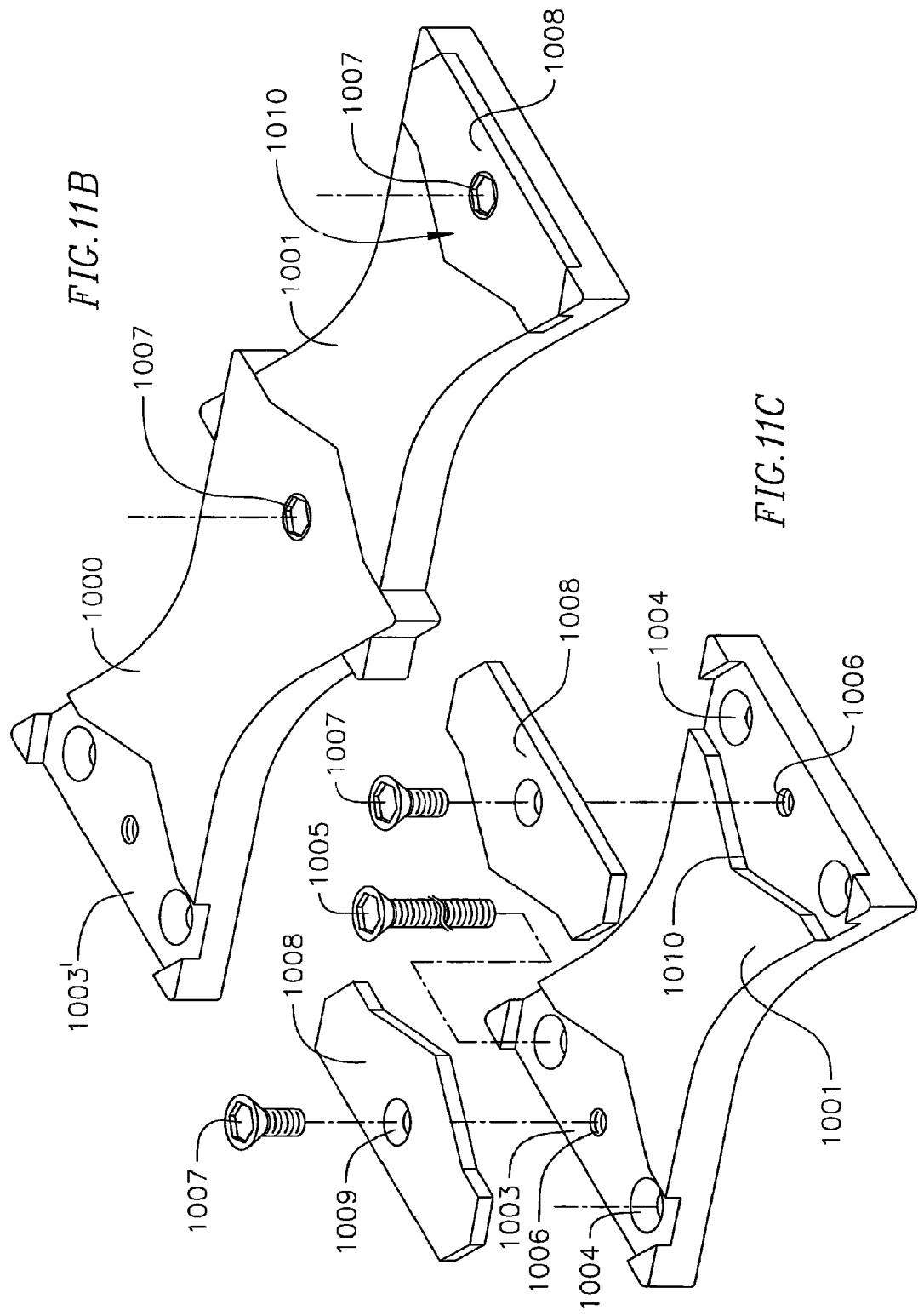

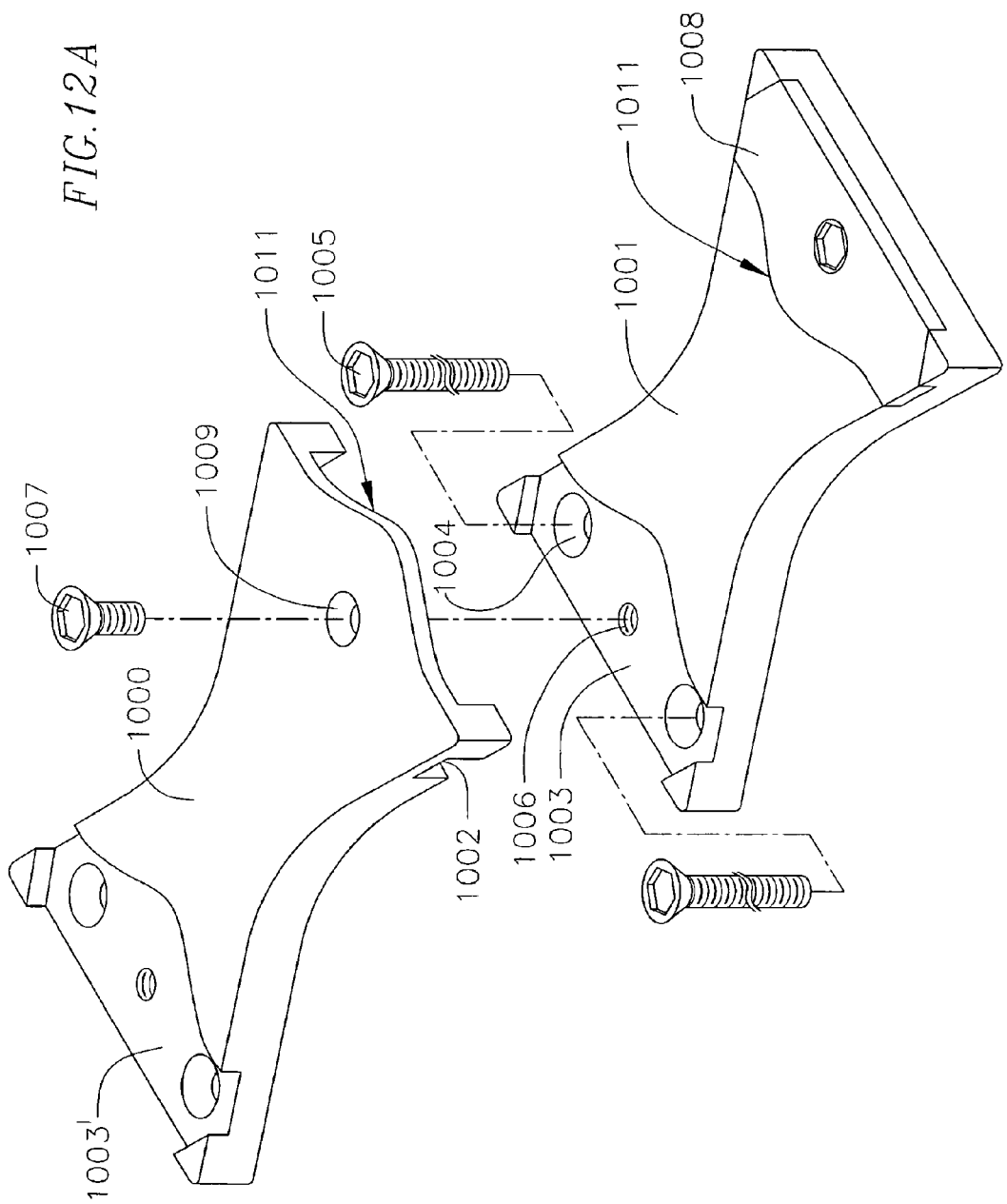

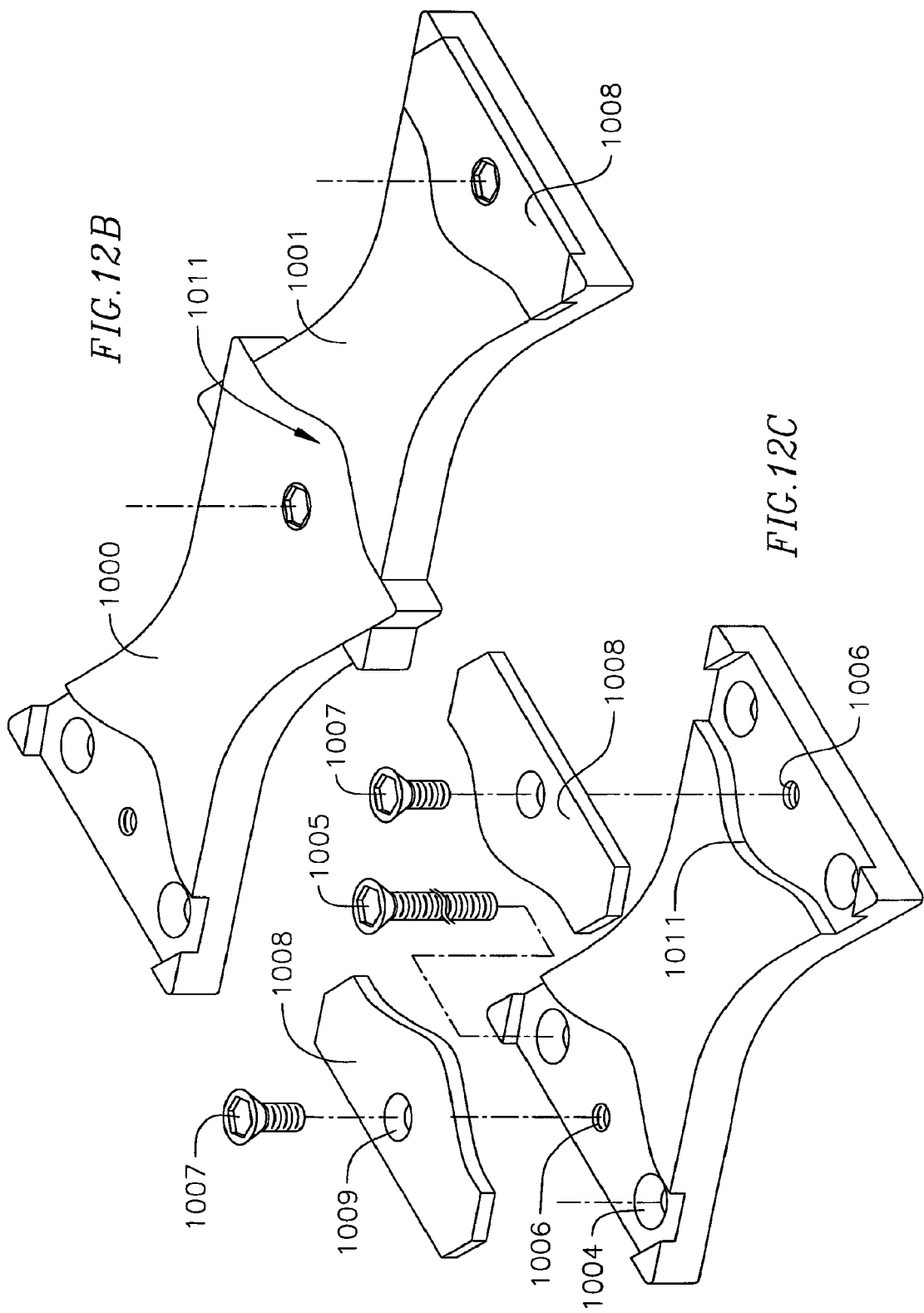

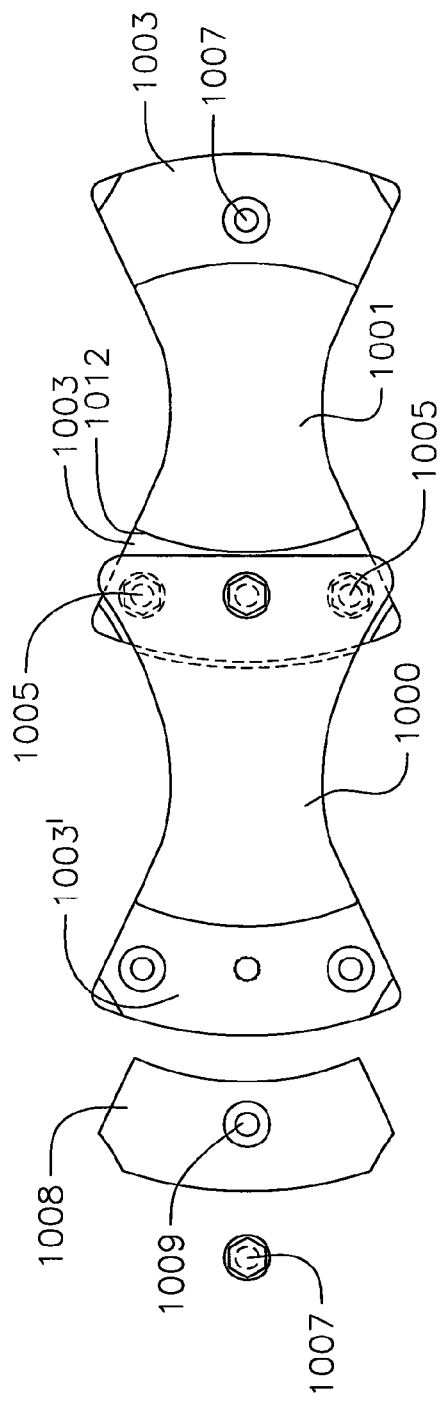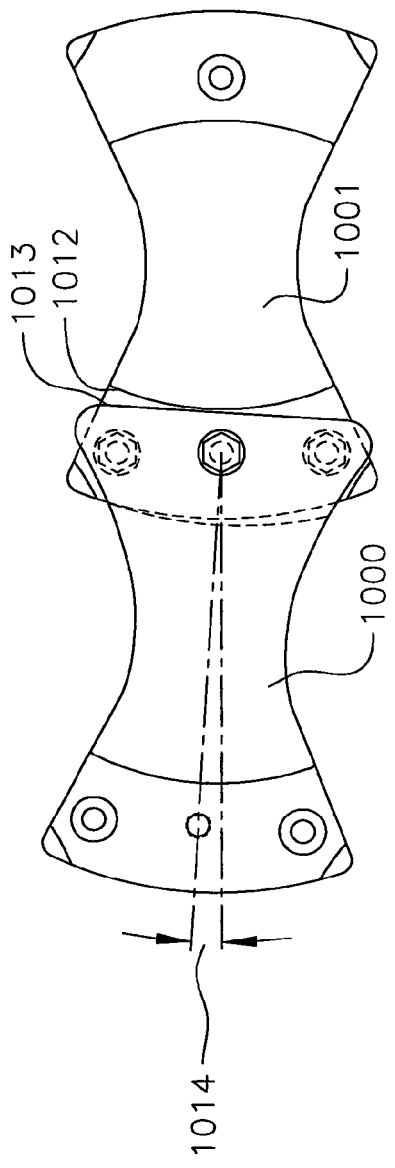

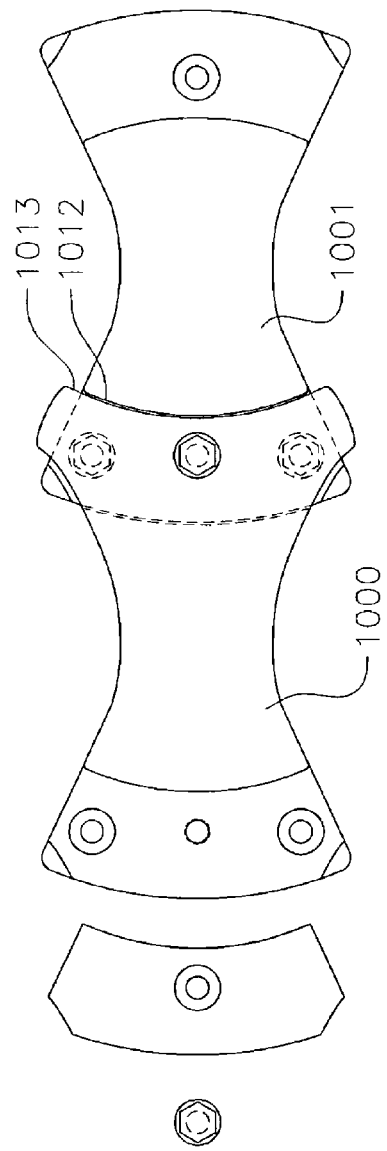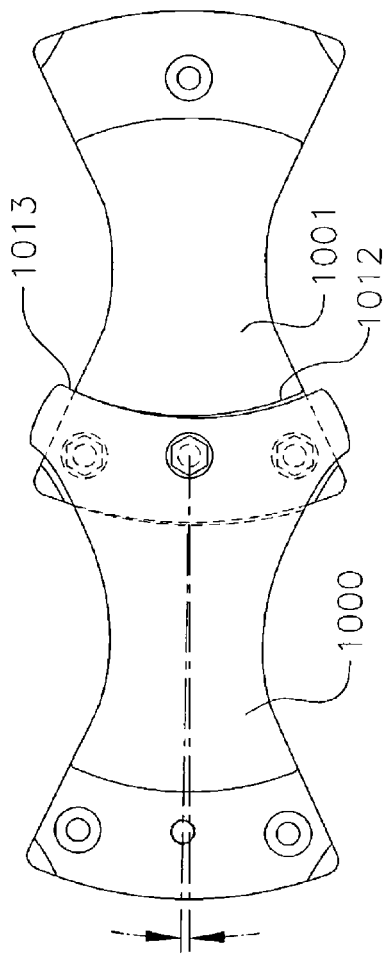

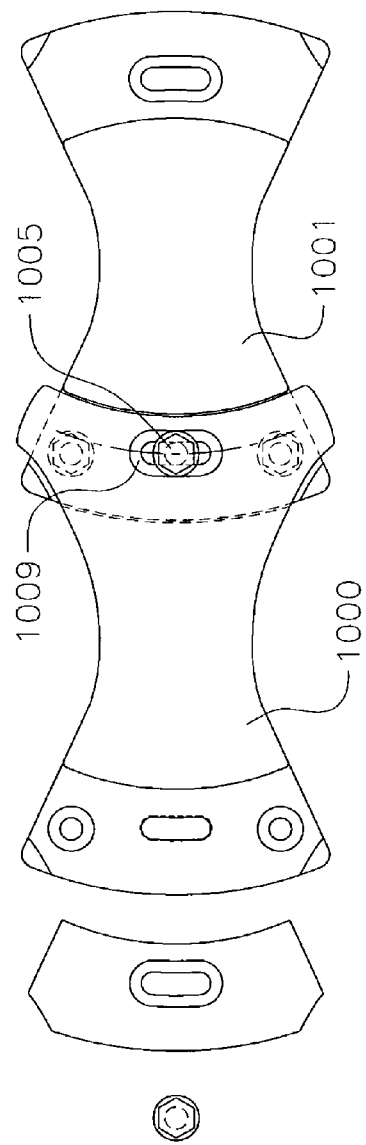
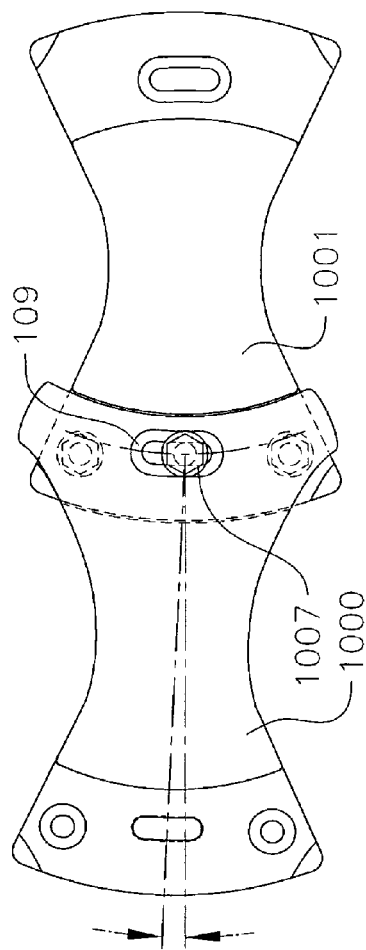

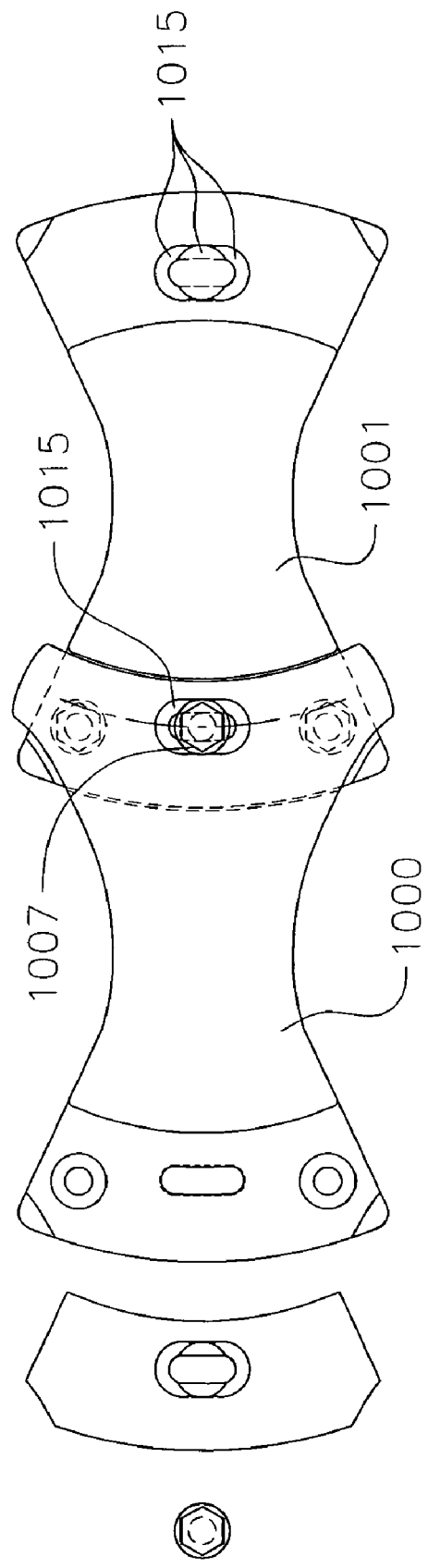

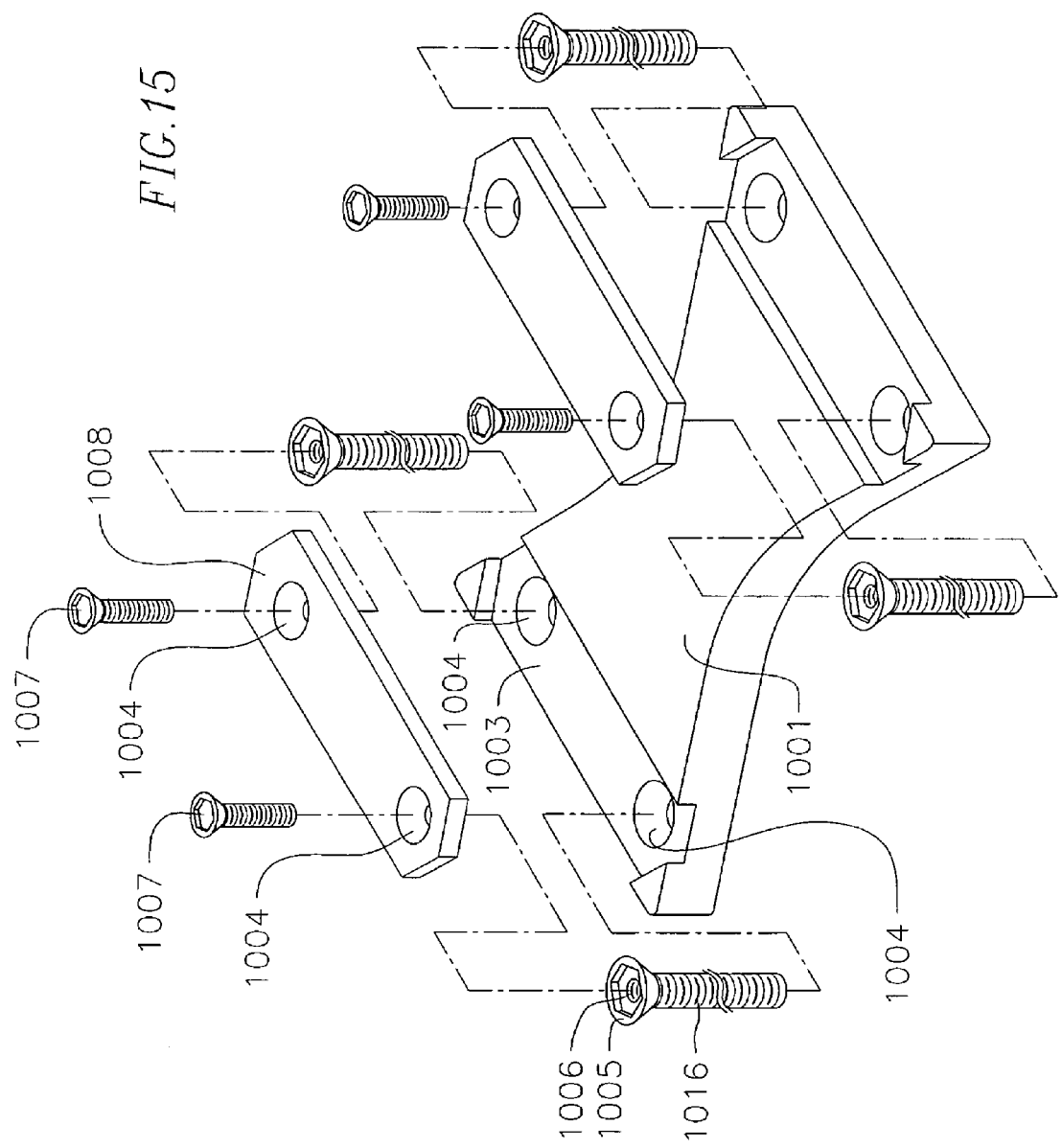

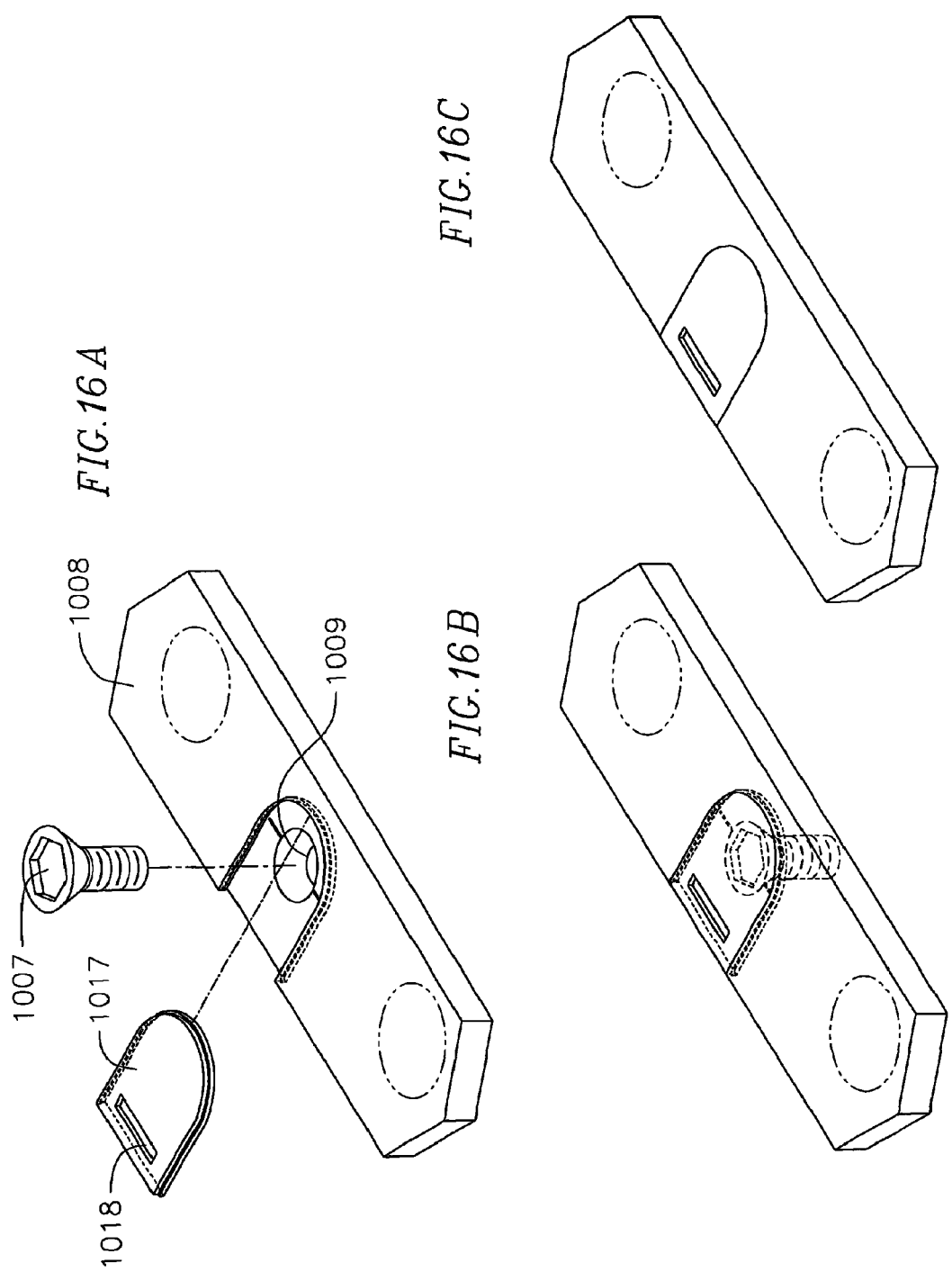

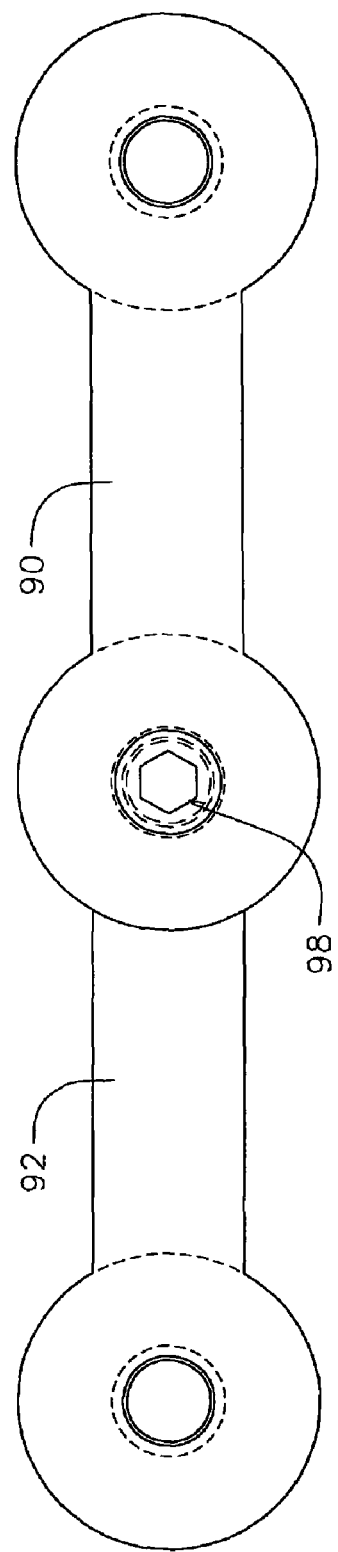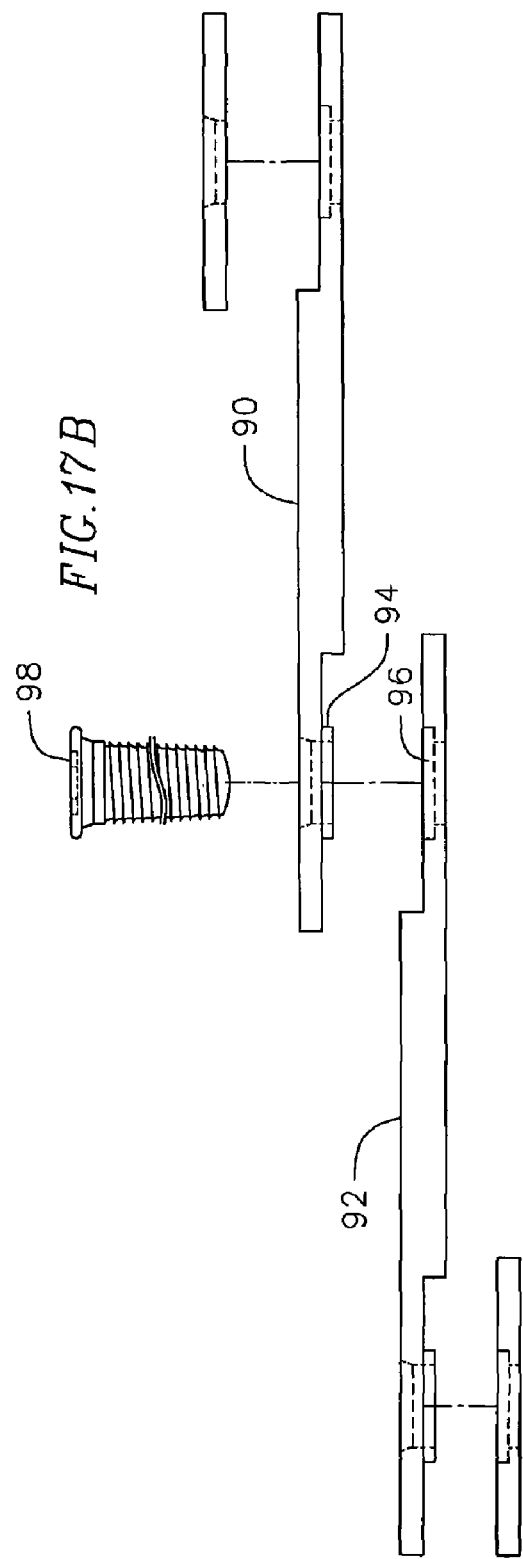

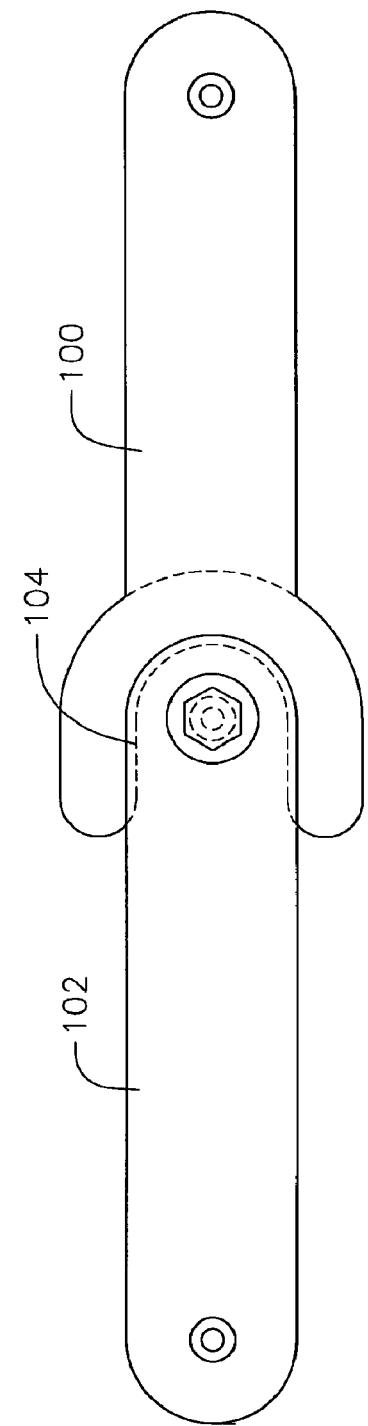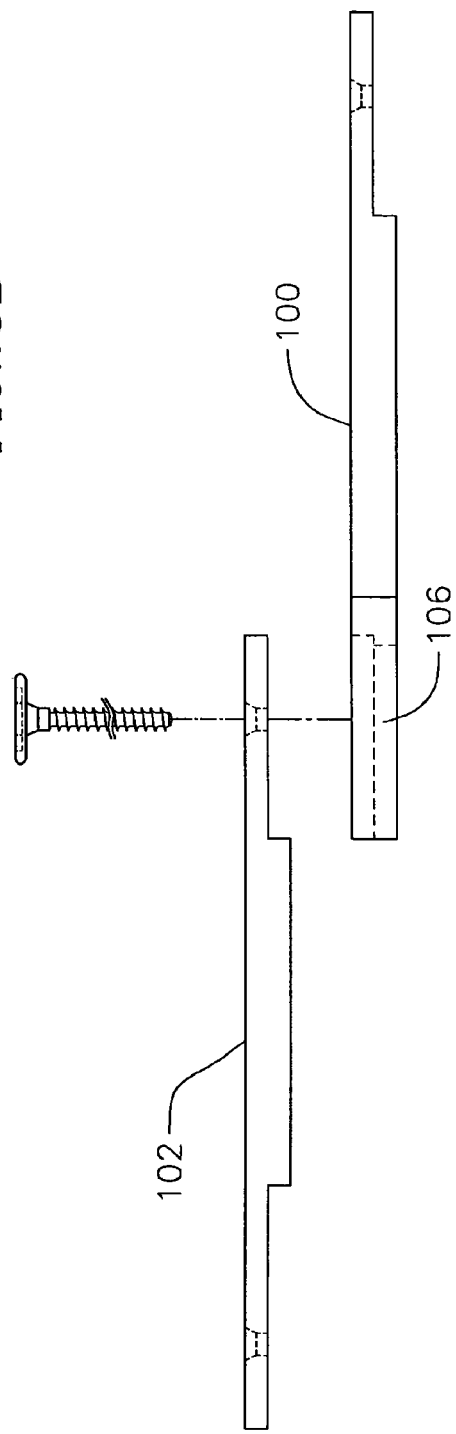

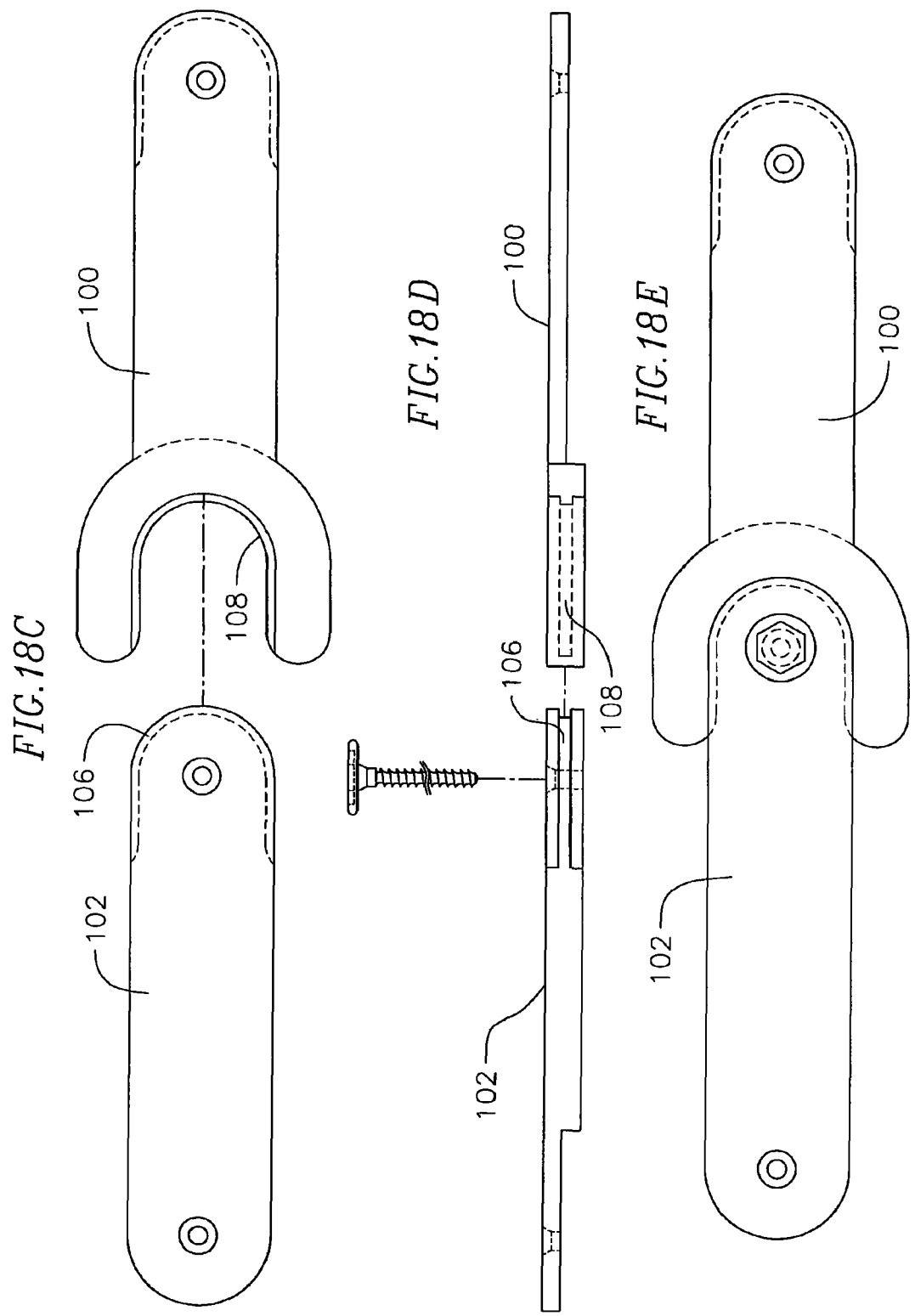

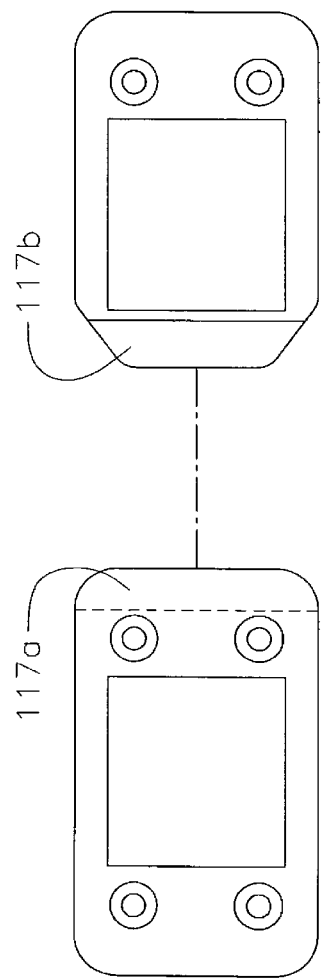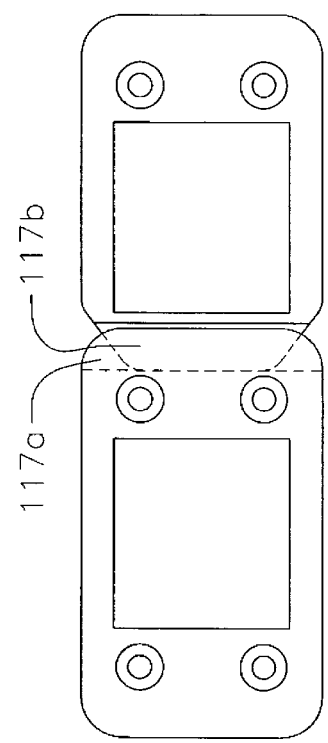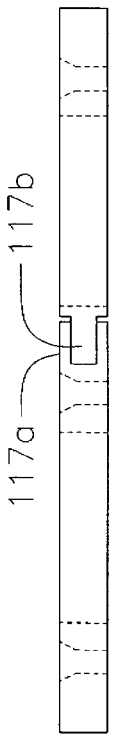

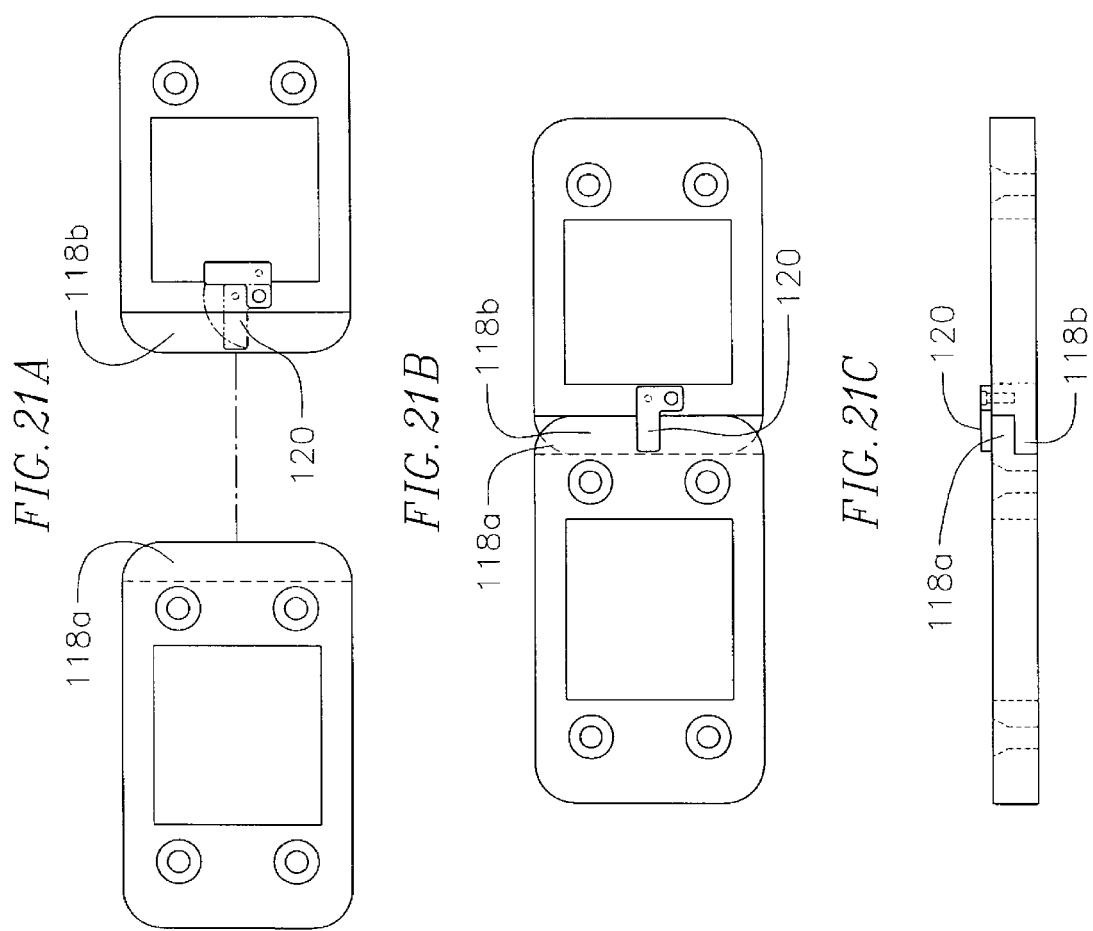

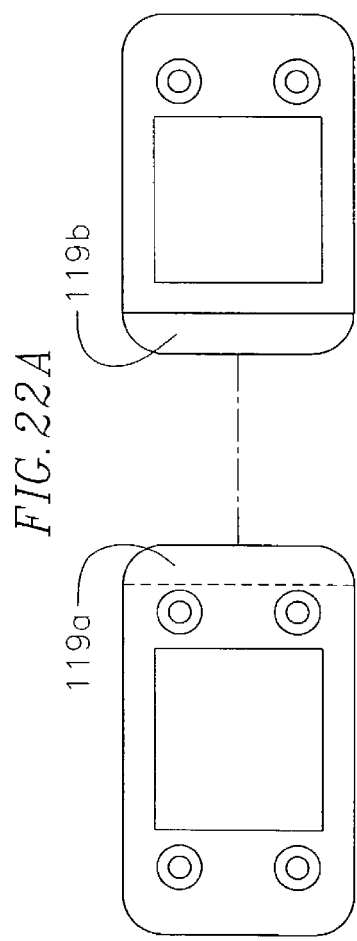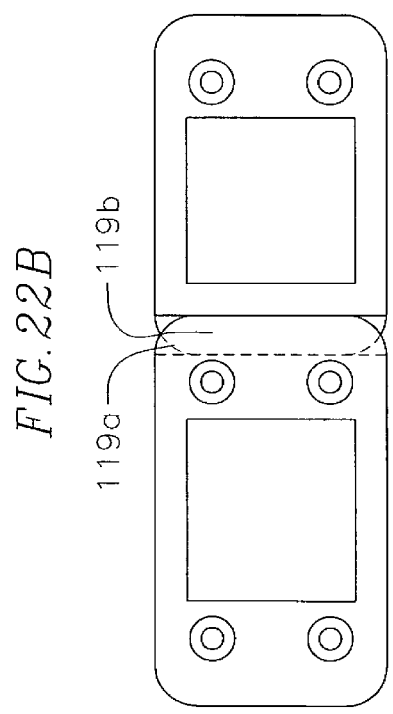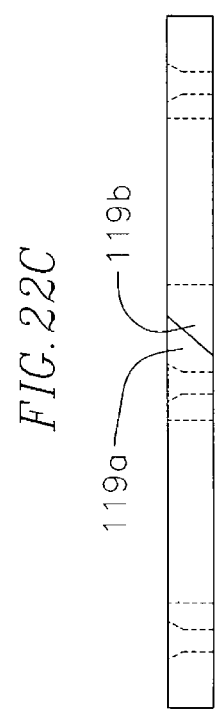

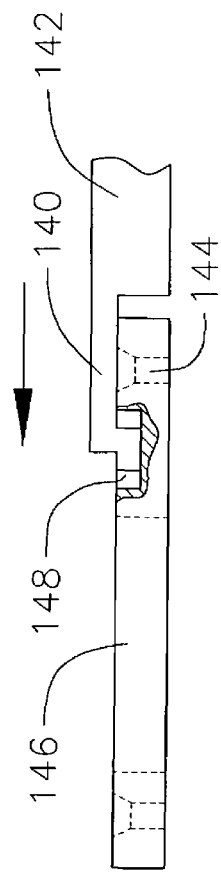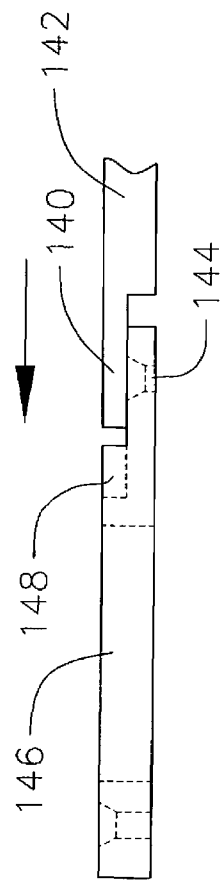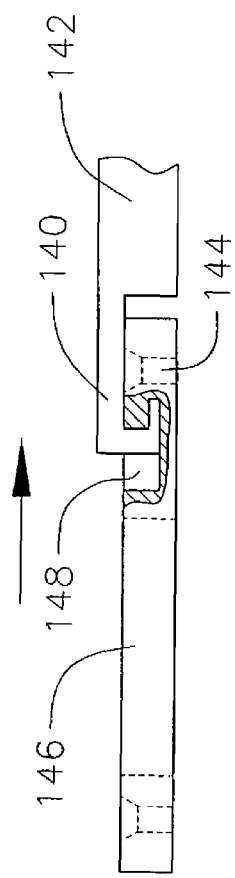

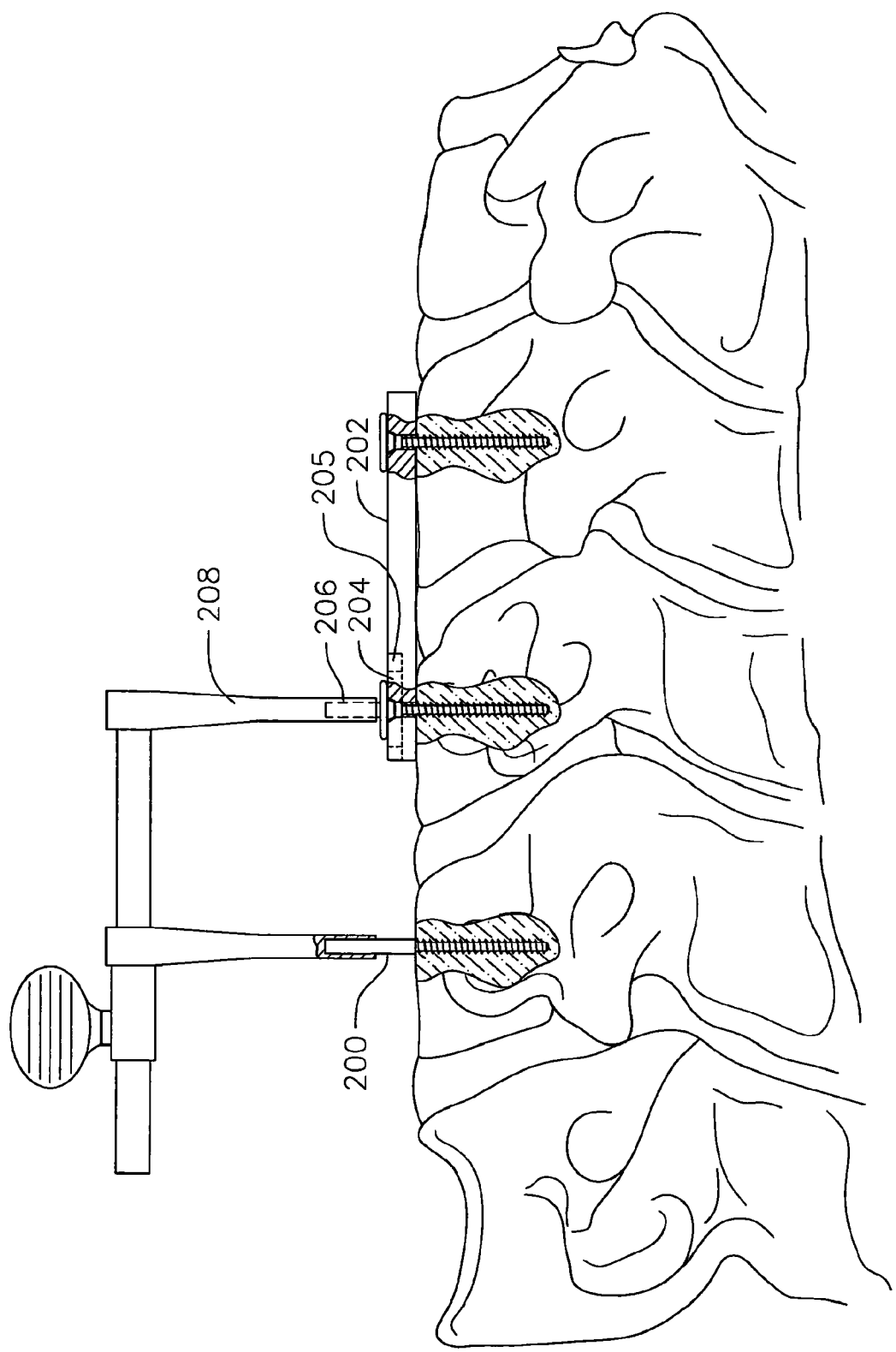

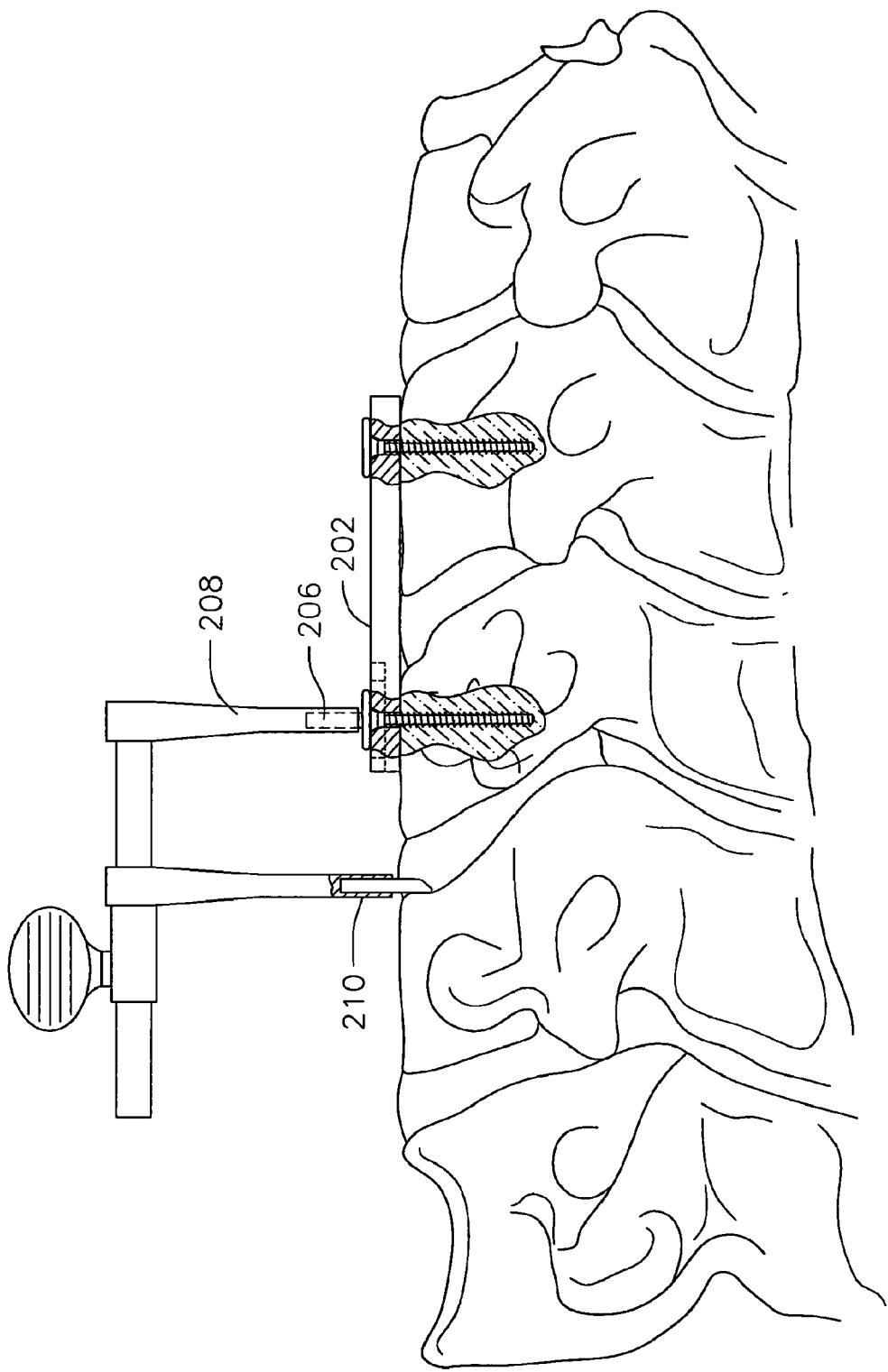

REVISABLE ANTERIOR CERVICAL PLATING SYSTEM

CROSS-REFERENCE TO RELATED APPLICATIONS

The current application is a continuation-in-part of U.S. patent application Ser. No. 11/417,794, filed May 3, 2006, which itself claims priority to U.S. Provisional Patent Application No. 60/680,728, filed May 12, 2005, the disclosures of which are incorporated herein by reference.

FIELD OF THE INVENTION

The current invention is related to an improved anterior cervical plating system; and particularly to a new method of interconnecting anterior cervical plates.

BACKGROUND OF THE INVENTION

Anterior cervical plating systems are well known, and there are a number of different such systems on the market. All currently available plating systems use a metal, usually titanium although any suitable surgical material may be used, plate, screws which go through the plate into the vertebra, and a locking mechanism, whereby the screw is locked to the plate. Locking is accomplished by a variety of mechanisms; a CSLP (a smaller central screw expands the head of the bone screw to lock it into the plate), a lock washer or press fit which locks the screw into the plate, or a locking device attached to the plate which is applied to the screw after it has been tightened. These designs include cams, washers, plates and screw-on caps applied to the plate after the screw has been engaged. Initial plate designs were rigid, but this led to the concept of stress shielding, and it was felt that rigid plates prevent loads from being transmitted through bone grafts, which can interfere with fusion and allow for grafts to be reabsorbed.

Although a substantial number of different plate designs have been developed, few of these systems adequately address a difficult surgical problem, revision surgery. Revision surgery is required in a patient who has already had an anterior cervical fusion, and who develops adjacent level disease. With current anterior cervical plating systems it is necessary to remove the previous plate in order to operate on the additional level. If a patient has had multiple levels done, the prior plate must come off of all of the previous levels in order to plate the previously unoperated adjacent level This is difficult surgically, and is associated with increased operative morbidity.

Accordingly, a need exists for an improved anterior cervical plating system with improved interconnectivity such that revision surgery is less intensive and traumatic to the patient.

SUMMARY OF THE INVENTION

The current invention is directed to an improved anterior cervical plate that allows a new plate to be attached to the prior plate, so that the old plate does not have to be removed.

In one embodiment, the anterior cervical plating system of the current invention includes a pre-positioned cervical plate having vertebral anchoring means and at least one base interlocking portion integrated therein. In such an embodiment the base interlocking portion is designed to engage a revision cervical plate, the revision cervical plates having its own vertebral anchoring means, an additional integrated base interlocking portion and an additional integrated cooperative interlocking portion. Regardless of the actual design of the interlocking portions, each of the base interlocking portions is designed to cooperatively engage each of the cooperative interlocking portions to provide a stabilizing interconnection between two adjacent plates, the stabilizing interconnection being capable of resisting movement of the adjacent cervical plates in at least one dimension, and wherein the operation of said stabilizing interconnection is independent of the operation of the vertebral anchoring means.

In another embodiment the system of the current invention uses at least one vertebral screw as the vertebral anchoring means.

In still another embodiment, the system of the current invention uses a channel integrally formed into at least one of the distal or proximal end of each of the cervical plates as the base interlocking portion. In such an embodiment, the cooperative interlocking portion comprises an armature interlockingly cooperative with the channel.

In yet another embodiment, the system of the current invention, the channel and the armature further include a pair of cooperative grooves and that interlock to prevent movement of the armature relative to the channel in at least one dimension. In such an embodiment, the grooves may be disposed in any confirmation, such as longitudinally along at least a portion of the sides of the armature and the channel, or alternatively, along at least a portion of the opposing faces of the armature and the channel.

In still yet another embodiment, the system of the grooves may further include at least one barb formed therein such that when the armature is drawn past the barb, said barb prevents further movement of the armature in at least one direction along said groove.

In still yet another embodiment, the armature may attach into the channel from any direction including either parallel or perpendicular to the longitudinal axis of the channel.

In still yet another embodiment, the armature and the channel are designed to cooperatively taper such that when the armature is drawn longitudinally away from the center of the channel the tapers interlock to prevent motion of the armature relative to the channel in at least one dimension. In such an embodiment, the channel is bidirectional that tapers both proximally and distally from the center of the plate.

In still yet another embodiment, the channel and armature further include a series of cooperative teeth formed crosswise across at least a portion of the opposing faces of the channel and armature.

In still yet another embodiment, the armature is formed by two parallel rails separated by a gap. In such an embodiment, the rails may be dynamically inwardly deformable. In still yet another such embodiment, the channel may further include a locking screw positioned to fit within the gap between the rails of the armature such that when tightened the locking screw locks the armature into the channel to prevent movement of the armature relative to the channel.

In still yet another embodiment, the armature interlocks with the channel by at least partially engaging the outer surface of the plate. In such an embodiment, the channel and armature may be interlocking mirror images. In still yet another such embodiment, the revision plate is attached to the original plate through a separate anchoring screw such that the vertebral screws on the original plate are left in place.

In still yet another embodiment, an external gripping plate may be designed to allow for an angular adjustment to the axis of the revision plate.

In still yet another embodiment, the cervical plates use a maximum of two vertebral anchoring means and cervical plate shares at least one vertebral anchoring means with an adjacent plate. In such an embodiment, the shared vertebral anchoring means may be disposed to engage both the armature and the channel of the adjacent plates. In still yet another such embodiment the channel may be formed with at least one external surface of the cervical plate and the armature has a cooperative groove and is formed to engage the external surface of adjacent cervical plate.

In still yet another embodiment, the revision plate may include at least two additional independent vertebral anchoring means.

In still yet another embodiment, the armature and channel are formed on the opposing lateral faces of the adjacent cervical plates and buttress against each other. In such an embodiment, the armature and channel may be formed in any suitable form including as a set of cooperative grooves, as a pair of cooperative stepped surfaces, and as a pair of interference fit surfaces, for example.

In still yet another embodiment, the armature and channel may be linked by a separate flexible band of material.

In still yet another embodiment, the cervical plates further include a removable cap for protectively covering base interlocking portion of the cervical plate when the base interlocking portion is unengaged with a corresponding cooperative interlocking portion.

In still yet another embodiment, the cervical plates further include an opening formed in the body of the plate disposed such that the opening overlaps and allows visual inspection of the disc space between two adjacent vertebra when said cervical plate is anchored in position.

In still yet another embodiment, the system further includes a distraction device designed to interlock with the integrated base interlocking portion of a cervical plate In still yet another embodiment, the invention is directed to a method of performing an anterior cervical fusion utilizing the inventive anterior cervical plating system.

BRIEF DESCRIPTION OF THE DRAWINGS

These and other features and advantages of the present invention will be better understood by reference to the following detailed description when considered in conjunction with the accompanying drawings, which are shown in schematic form, wherein:

FIGS. 1a to 1f are directed to a first embodiment of an anterior cervical plating system according to the current invention.

FIGS. 2a to 2h are directed to a second embodiment of an anterior cervical plating system according to the current invention.

FIGS. 3a to 3e are directed to a third embodiment of an anterior cervical plating system according to the current invention.

FIGS. 4a to 4e are directed to a fourth embodiment of an anterior cervical plating system according to the current invention.

FIGS. 5a to 5f is directed to a fifth embodiment of an anterior cervical plating system according to the current invention.

FIGS. 6a to 6e are directed to a sixth embodiment of an anterior cervical plating system according to the current invention.

FIGS. 7a to 7f are directed to a seventh embodiment of an anterior cervical plating system according to the current invention.

FIGS. 9a to 9c are directed to a ninth embodiment of an anterior cervical plating system according to the current invention.

FIGS. 10a to 10c are directed to an alternative embodiment of the embodiment of the anterior cervical plating system in accordance to the current invention provided in FIG. 9.

FIGS. 11a to 11c are directed to an alternative embodiment of the embodiment of the anterior cervical plating system in accordance to the current invention provided in FIG. 9.

FIGS. 12a to 12c are directed to an alternative embodiment of the embodiment of the anterior cervical plating system in accordance to the current invention provided in FIG. 9.

FIGS. 13a to 13g are directed to an alternative embodiment of the embodiment of the anterior cervical plating system in accordance to the current invention provided in FIG. 9.

FIG. 15 is directed to an alternative embodiment of the embodiment of the anterior cervical plating system in accordance to the current invention provided in FIG. 9.

FIGS. 16a to 16c are directed to an alternative embodiment of the embodiment of the anterior cervical plating system in accordance to the current invention provided in FIG. 9.

FIGS. 17a and 17b are directed to a tenth embodiment of an anterior cervical plating system according to the current invention.

FIGS. 18a to 18e are directed to a eleventh embodiment of an anterior cervical plating system according to the current invention.

FIGS. 20a to 20c are directed to a thirteenth embodiment of an anterior cervical plating system according to the current invention.

FIGS. 21a to 21c are directed to a fourteenth embodiment of an anterior cervical plating system according to the current invention.

FIGS. 22a to 22c are directed to a fifteenth embodiment of an anterior cervical plating system according to the current invention.

FIGS. 25a to 25g are directed to a eighteenth embodiment of an anterior cervical plating system according to the current invention.

FIGS. 26a to 26d are directed to an embodiment of a distraction system for use with an anterior cervical plating system according to the current invention.

DETAILED DESCRIPTION OF THE INVENTION

Figure 1E:
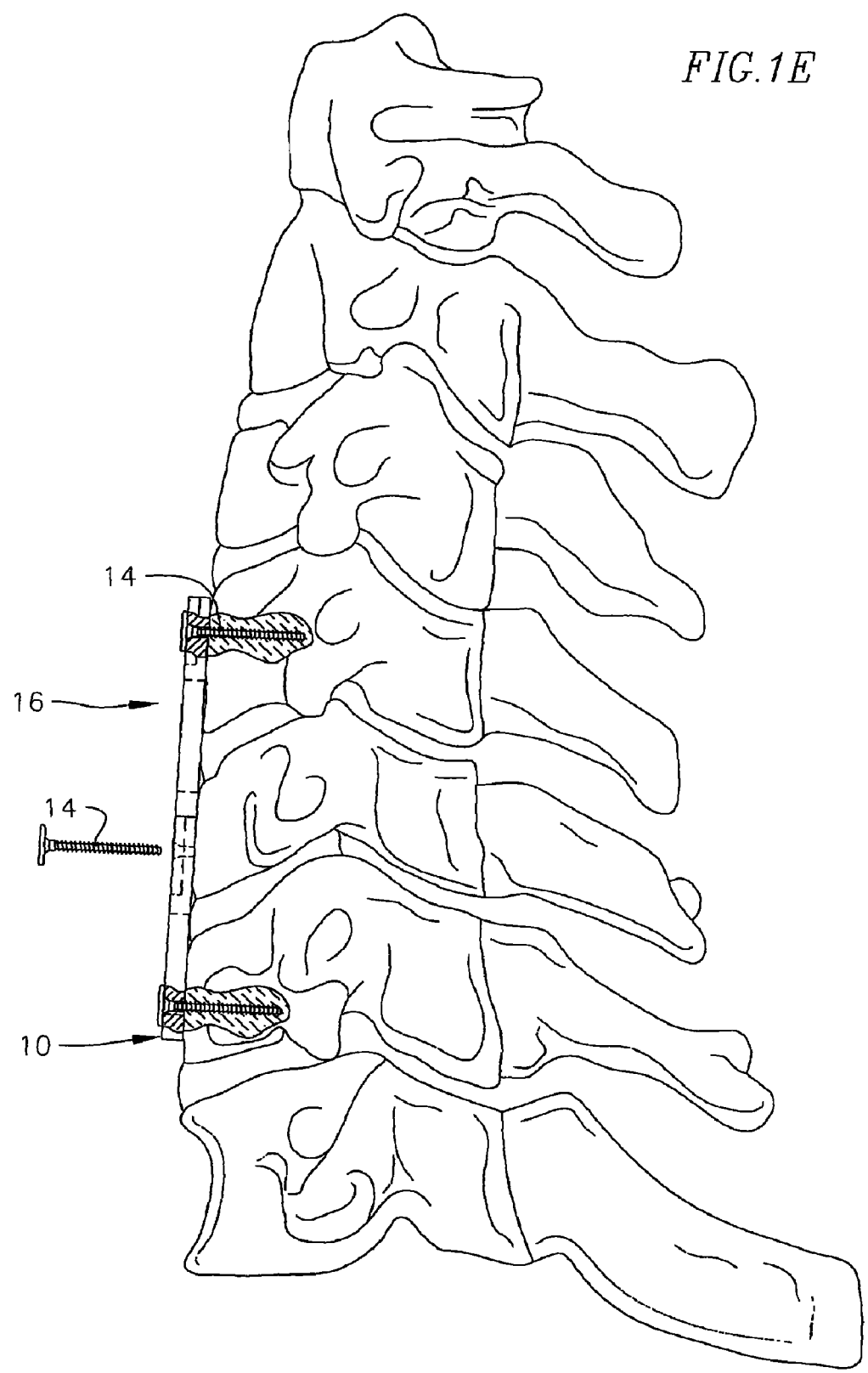
Figure 1F:
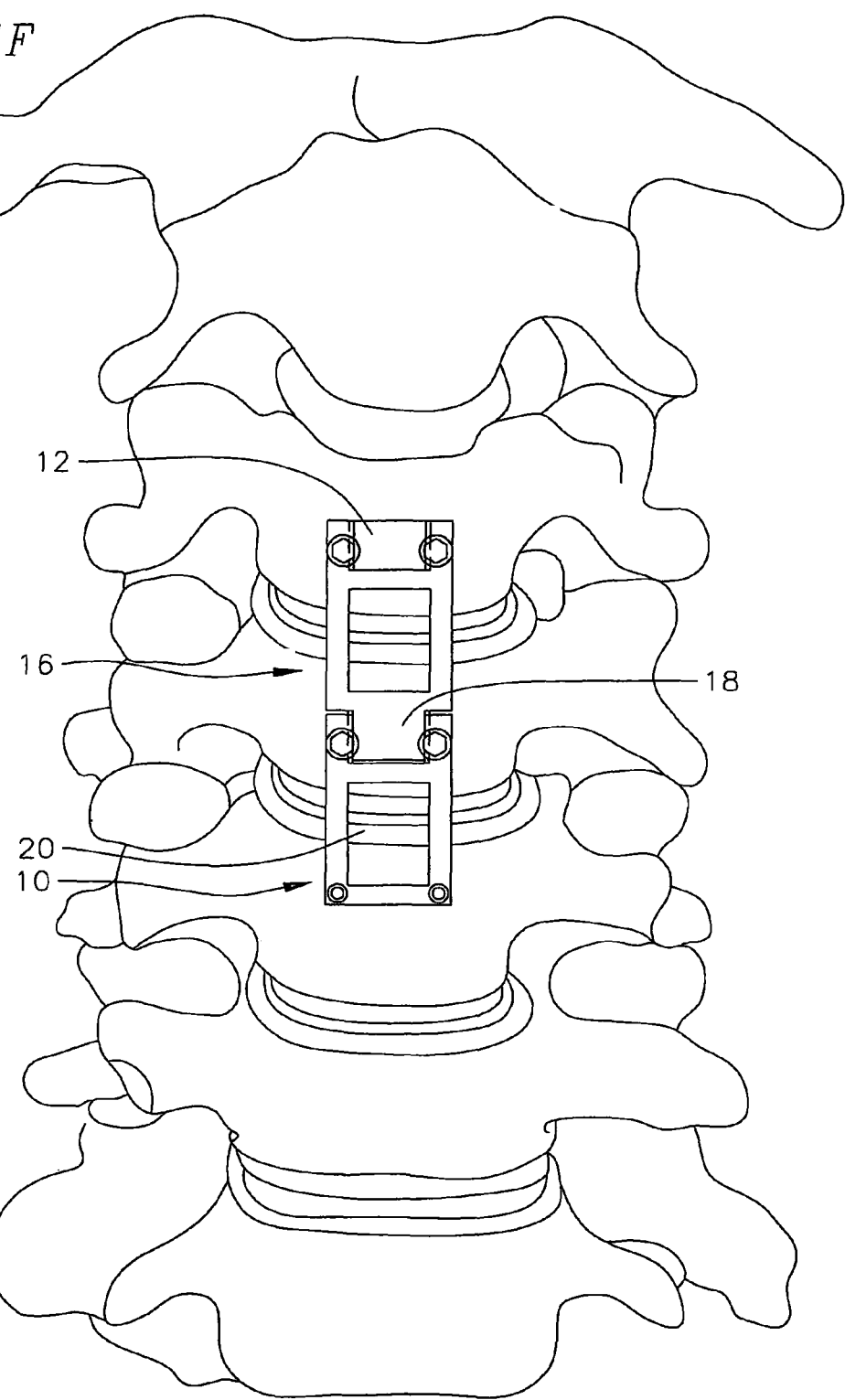

The current invention is directed to an improved revisable anterior cervical plate system that allows for a new plate to be attached and integrated into the prior plate, such that the old plate does not have to be removed during a revision surgery.

Although the figures and following discussion will provide a detailed description of a number of exemplary embodiments of the cervical plate system of the current invention, it should be understood that any number of designs can be used to achieve the basic goal of the system. For example, in their basic form each of the exemplary plating systems include an existing plate and a revision plate each designed to be anchored to a vertebral bone through a vertebral anchoring means, such as, a connecting screw. A characteristic feature of this plate system is that each of the revision plates includes an interlocking portion that provides a linkage between the plates. The linkage can be either flexible or rigid, of any suitable design such that the two plates can be lockingly connected without removal of the existing plate. These linkages in turn can be locked rigidly between the plates (in a so-called fixed system), or can be allowed to travel to a limited degree to allow for settling (in a so-called dynamic system). The choice of whether to use a fixed or dynamic system is left to the surgeon.

In addition, it should be understood that the figures are merely schematic, and that the relative dimensions of the various elements and their relative spacings are merely exemplary and could be varied by one of ordinary skill in the art while remaining within the bounds of this disclosure. For example, the size and spacing of the vertebral anchoring means (e.g., the vertebral screws), as well as the placement and sizing of the interlocking mechanism could be varied such that more substantial screws with more limited spacing there between could be used. Likewise, the overall shape and dimensions of the plates could be altered to allow the revision system of the current invention to conform with any currently available cervical plating system.

Regardless of the ultimate design, both the original and the revision plates of the current invention are constructed as an integrated plate system such that the interlocking portion of the revision plate cooperates with the base interlocking portion of the original plate. These interlocking portions have coordinating surfaces that lock the two plates together and provide torsional stability to and between the plates in at least one dimension that is independent of the connecting screws.

Several variants of this basic design are shown in FIGS. 1 to 16, all of which incorporate the basic innovation of having a linkage system that both allows a new plate to be securely fixed to a preexisting plate and has coordinating surfaces between the old and new plates that when combined provide stability to and between the plates independent of the vertebral connecting screws.

In one example these interlocking portions (linkages and coordinating surfaces) take the form of a dovetail slider. A dovetail slider can be formed in a number of different ways and roughly resembles a cabinet-style joinery. In FIGS. 1a to 1f an embodiment of a stackable cervical plating system of the current invention having a simple groove and joint dovetail slider system is shown. In this embodiment, as shown in FIGS. 1a to 1d, the pre-installed plate (10), which has previously been affixed to the anterior cervical spine has a groove (12) running between two mounting screws (14), and the new plate (16) has a corresponding linkage arm (18), which inserts into the groove (12) of the old plate (10) between the two screws (14). Top-views (FIGS. 1a and 1b), a cross-sectional view (FIG. 1c), and a profile view (FIG. 1d) of these exemplary plates are provided. As shown by the cross-sectional view provided in FIG. 1c, the groove is cut such that the linkage can only move in a single dimension along the longitudinal axis of the original plate thereby providing stability to and between the plates in all other flexural directions.

In addition to this inherent stability provided by the linkage/groove design, as shown in FIGS. 1a and 1b, the screws (14) overlap the groove (12) of the old plate (10). As a result of this geometry, once the arm (18) of the new plate (16) has been inserted into the groove of the old plate, the new plate can either be locked into a fixed position by tightening the overlap screws, or the screws can be left loose to allow the new plate to settle providing a dynamic plate system. Schematic diagrams of this embodiment of the invention installed on the spine of a patient are further provided in FIGS. 1e and 1f. Although similar views are not provided for each of the remaining exemplary plate systems, it should be understood that their installation on a patient would be identical.

In addition, as shown in FIGS. 1a, 1b, and 1d, an optional window (20) can be provided in the plate system to allow for the inspection of the disc space. Such a window is particularly valuable to observe any bone-graft material that might have been disposed within the space beneath the plate system.

In the above-embodiment, as well is in the embodiments that follow, it should be understood that the grooves and window cut-outs on the plates can optionally be provided with snap-in pieces that fill the grooves and cut-outs of the plates until such time as a new plate is needed. Such a filler piece would be advantageous to prevent the accumulation of bone or other organic matter within the groove or cut-out of the plate that might foul the working elements of the plate and prevent a successful interlock between the plates.

FIGS. 2a to 2h demonstrate an alternative embodiment of the basic dovetail configuration. As shown in FIGS. 2a and 2b, the old plate (22) has a grooved channel (24), which corresponds to a cooperative groove (26) on the interlock arm (28) of the new plate (30), such that when engaged by the new plate the grooved upper edge (24) of the old plate overlaps the cooperative groove (26) of the arm (28) of the new plate to provide a secure connection between the two plates. This groove and overlap mechanism allows the arm (28) of the new plate (30) to snap into position from and then to lock (as shown in FIGS. 2c to 2f) so that it may be positioned from above and does not have to be fed in parallel to the previously placed plate (22), as in the embodiment shown in FIG. 1. FIGS. 2g and 2h provide detailed cross-sectional diagrams of the grooved channel (24) of the old plate and arm (28) of the new plate, respectively.

Again, as discussed above, the interlocking grooves on the channel of the old plate and the arm of the new plate provide a linkage when engaged that can only be moved in a single dimension distally along the longitudinal axis of the original plate thereby providing stability to and between the plates in all other flexural directions. Although only simple groove profiles are shown in this embodiment, it should be understood that any groove profile suitable for interlocking the arm of the new plate with the old plate may be utilized. For example, a groove with a locking barb may also be used, which would allow for a locking snap fit of the new plate. In addition, as shown in all of the figures, this plate may also be equipped with a window (32) for the inspection of the disc space.

Figure 3A:
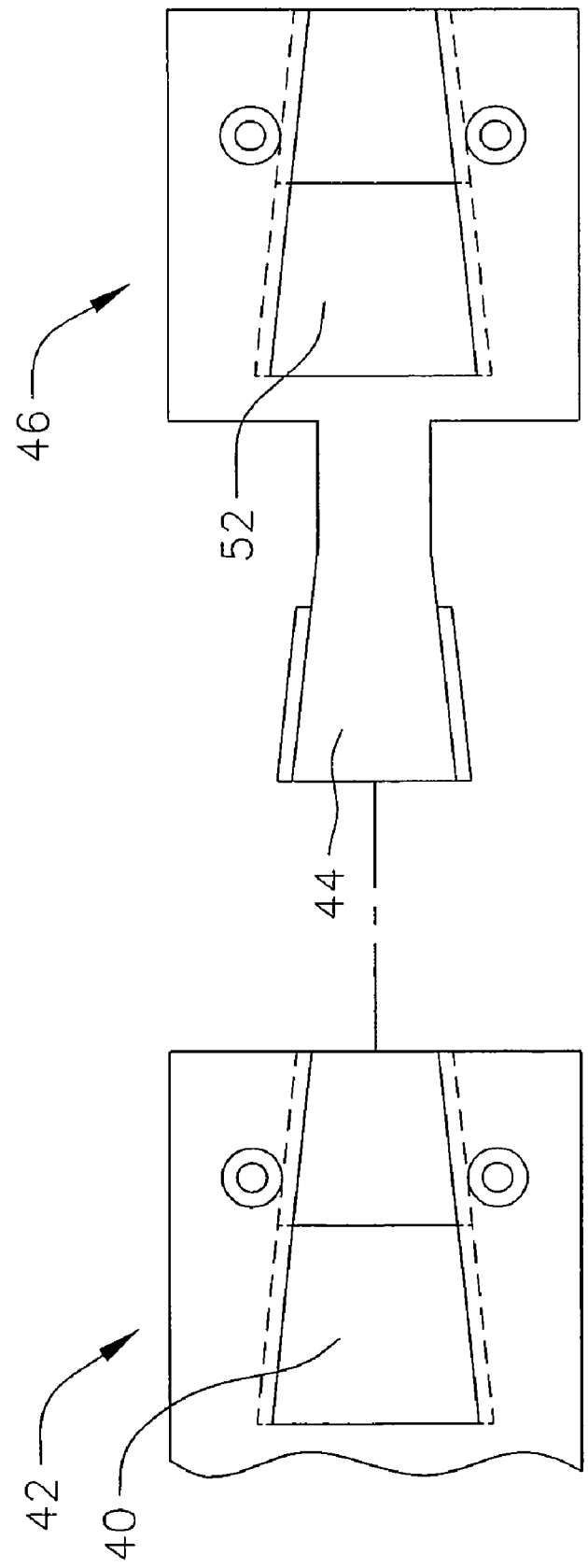
Figure 3B:
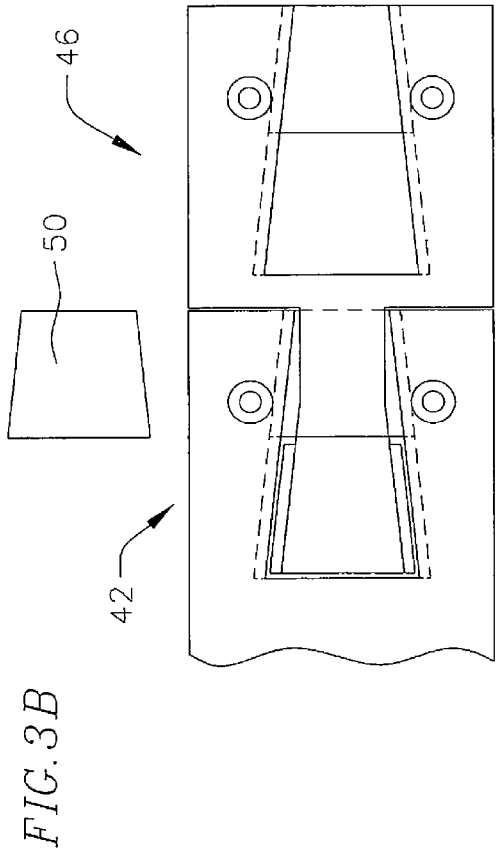
Figure 3C:
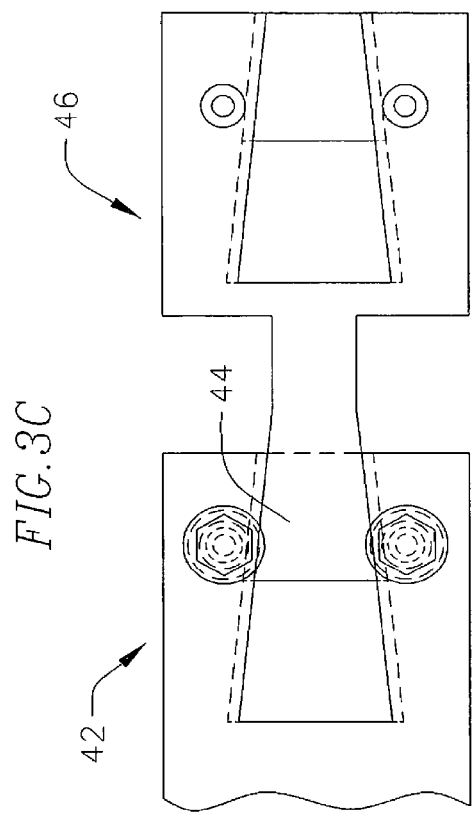

Collectively, FIGS. 3a to 3e depict another exemplary embodiment of the dovetail slider system in which the dovetail (as shown in FIG. 3a) is tapered to form a trapezoidal groove or channel (40) on the pre-installed plate (42) and an interlocking trapezoidal arm (44) on the new plate (46). Such a trapezoidal geometry again allows for the new plate to be moved into the groove from above and the locked into position (as shown in FIGS. 3b and 3c). In addition, the trapezoidal shape and the cooperative groove both operate together to provide a linkage that can only move in a single dimension distally along the longitudinal axis of the original plate thereby providing stability to and between the plates in all other flexural directions. Again although only standard grooves are shown in these embodiments, it should be understood that these linkages could also be provided with locking grooves to positively lock the arm of the new plate into position within the trapezoidal channel of the old plate.

FIGS. 3a to 3c, show only a single directional plate system, in which the trapezoidal window (40) only runs in one direction along the pre-installed plate, allowing for the addition of a new plate only on the side (or one level) of the pre-installed plate with the groove. However, as shown in FIGS. 3d and 3e, added flexibility can be achieve by providing a bidirectional channel (48) on the pre-installed plate. Such a bidirectional channel would allow for the addition of new plates on both adjacent levels of the spine.

As discussed above, the channel (40) within which the arm (44) of the new plate (46) rests can also be provided with a snap-in piece (50) that would be remove at the time the new plate is installed to ensure that the groove remains unfouled prior to surgery. In addition, as shown in FIGS. 3a to 3e, an optional window (52) can be provided in the plate system to allow for the inspection of the disc space.

In addition to grooves that lock the sides of the plate and prevent movement of the arm perpendicular to the longitudinal axis of the plate, as used in the embodiments depicted in FIGS. 1 to 3, as shown in FIGS. 4a to 4e, the linkage mechanism might also be provided with a mechanism for resisting the movement of the plate along that longitudinal axis. In the embodiment shown in these figures both the channel (54) of the old plate (55) and the arm (56) of the new plate (57) are provided with interlocking ridges or teeth (58 & 59, respectively), such that when the plates are engaged (as shown in FIG. 4e) the teeth in the channel of the old plate and the teeth on the arm of the new plate engage to lock the arm into position along the longitudinal axis of the plates.

Although not shown, as discussed above, the channel within which the arm of the new plate rests can also be provided with a snap-in piece that would be removed at the time the new plate is installed to ensure that the groove remains unfouled prior to surgery. In addition, as shown in the figures, an optional window can be provided in the plate system to allow for the inspection of the disc space.

FIGS. 5a to 5f depict yet another possible embodiment of the basic dovetail slider plate system. In this embodiment, the new plate (60) is provided with a pair of rails (62) rather than a central beam, each rail having a groove (63) that would interlock with the groove (64) of the channel (65) of the pre-installed plate (66). As shown in the cross-sectional views provided in FIGS. 5c and 5d, cooperative grooves both operate together to provide a linkage that can only move in a single dimension distally along the longitudinal axis of the original plate thereby providing stability to and between the plates in all other flexural directions. Again although only standard grooves are shown in these embodiments, it should be understood that these linkages could also be provided with locking grooves to positively lock the arm of the new plate into position within the trapezoidal channel of the old plate.

As with the embodiments shown in FIGS. 2 to 4, as shown in FIGS. 5e and 5f, this groove and overlap mechanism allows the rails of the new plate (62) to snap into position and then to lock as it is pulled backward so that it may be positioned from above and does not have to be fed in parallel to the previously placed plate (66). In addition to the groove shown, because the rails can flex inwardly, an expansion fit could also be used such that once disposed within the groove the rails would expand outwardly to press against the walls of the groove of the pre-installed plate. In such an embodiment, the rails could be made of a malleable metal such as nytinol, which would allow for a dynamic expansion fit.

Although not shown in FIG. 5, once in position within the old plate a number of mechanisms could be used to either exclusively or further lock the rails into position, including, for example, a center lock screw (68, as shown in FIGS. 6a to 6e), which could be placed between the rails at a locking position (69) to lock the new plate into its desired configuration. Other exemplary locking mechanisms include a top plate (not pictured) that would screw over the two plates, a slide lock groove (not pictured), or a block at the back of the rails (not pictured) that would prevent the rails from backing out of the groove of the pre-installed plate. All these locking mechanisms have the advantage that they could be added after the new plate has been positioned, and do not need to be pre-installed on the old plate.

In addition, as shown in FIG. 6c, the channel (65) within which the rails (62) of the new plate lock can also be provided with a snap-in piece (70) that would cover the grooves (64) and locking position (69) on the pre-positioned plate prior to installation of the new plate to ensure that the groove remains unfouled prior to surgery. In addition, as shown in the figures, an optional window (72) can be provided in the plate system to allow for the inspection of the disc space.

Although the interlocking mechanism of the coordinating surfaces on the embodiments discussed thus far (i.e., the grooves) have been situated on the sides of the coordinating surfaces. In yet another embodiment, as shown in FIGS. 7a to 7f the interlocking mechanism is positioned along the faces of the coordinating surfaces. For example, as shown in FIGS. 7a to 7c, in one embodiment, the pre-positioned plate has a groove 80 cut into the face of the coordinating channel surface 76, and the new plate (75) has a cooperative undercut (82) formed on the underside of the interlocking arm (78). As shown in FIGS. 7d to 7f, this and overlapping groove mechanism allows the arm (78) of the new plate (75) to snap into position from above and then to lock as it is pulled proximal to the new plate so that it may be positioned from above and does not have to be fed in parallel to the previously placed plate (74).

Again, as discussed above, the interlocking grooves on the channel of the old plate and the arm of the new plate provide a linkage when engaged that can only be moved in a single dimension distally along the longitudinal axis of the original plate thereby providing stability to and between the plates in all other flexural directions. Although only simple groove profiles are shown in this embodiment, it should be understood that any groove profile suitable for interlocking the arm of the new plate with the old plate may be utilized. For example, a groove with a locking barb may also be used, which would allow for a locking snap fit of the new plate. In addition, as shown in all of the figures, this plate may also be equipped with a window (83) for the inspection of the disc space.

Figure 8A:
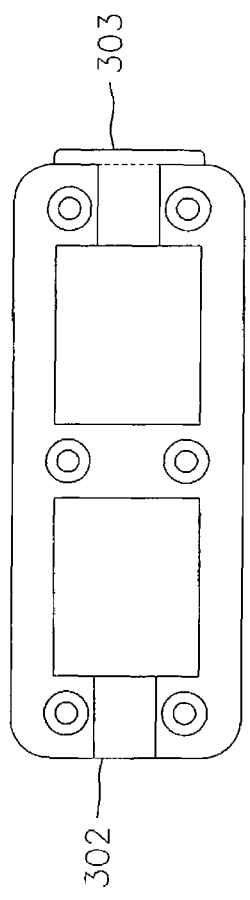
FIGS. 8a to 8d are directed to an eighth embodiment of an anterior cervical plating system according to the current invention.
Figure 8B:
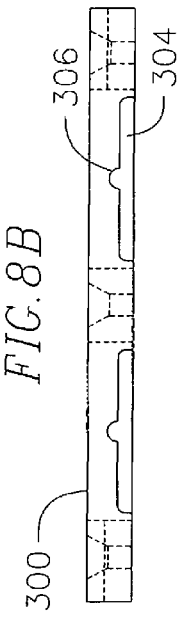
Figure 8C:
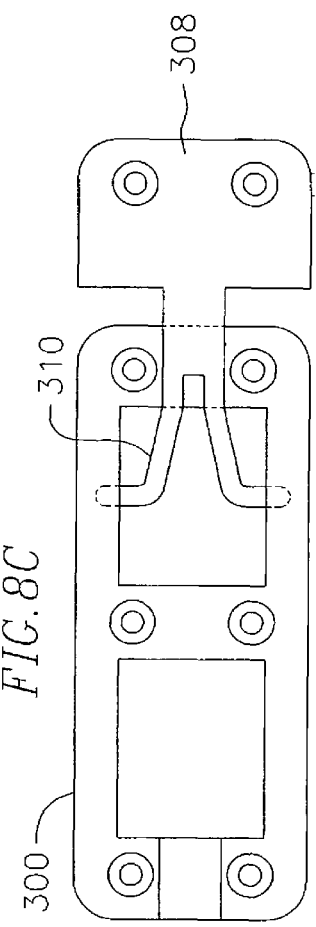
Figure 8D:
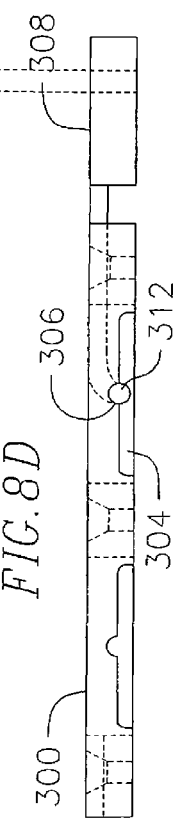

Although the above-discussed plating systems have mechanisms designed to engage the inner surfaces of the plate, it should also be understood that the system of the current invention may also be designed to engage the underside of the plate. One exemplary embodiment of such a system shown in FIGS. 8a to 8d has an interlocking mechanism that takes advantage of corrugations on the undersurface of a plate. As shown in FIG. 8a, as with many of the plates described above the system generally includes a pre-positioned plate (300) that includes a channel (302) that can include a removable snap-in or removable blocker (304) on one or two ends of the plate. However, as FIG. 8b shows, in this system, the underside of the plate has an undercut (304) that includes an interlocking indention (306). As shown in FIGS. 8c and 8d, when linked with a revision plate (308), the resilient arms of the cooperative interlocking mechanism (310) bend through the channel (302) and then spring into position in the interlocking indentions (306) in the undercut (304) on the underside of the pre-positioned plate (300). Such a system can provide an interlinking system for radically undercut plating systems, such as, for example, bendable plates that are too thin to allow further channeling in the top surface of the plate.

Figure 9A:
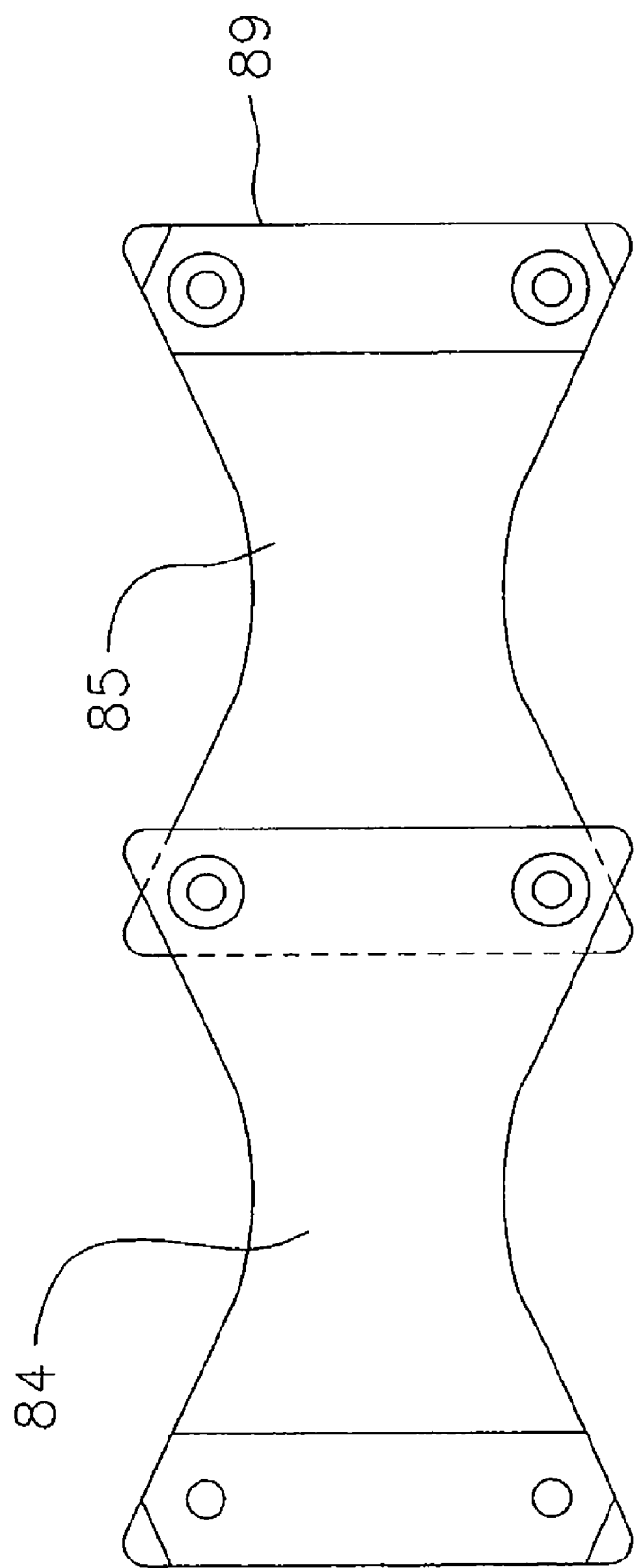

In addition, although all of the cooperatively interlocking configurations previously discussed involve the use of systems in which the attachment point between the pre-positioned plate and the new plate is internal to the plate, it should be understood that any suitable attachment mechanism may be used. For example, the embodiment of the inventive cervical plate system provided in FIGS. 9*a* to 9*c*, shows a plate system having a coupling groove on the external side of the plate. As shown in the figure, in this embodiment the two plates (85 and 86) have cooperative recesses (87 and 88) which engage each other to form an integrated plate. As shown in FIG. 9*c*, when interlocked the two plates would form a common passage (89) through which vertebral attachment screws would be passed. Although not shown, such a system could also be provided with groove locks on the edges to the plate, such as those discussed in relation to the other dovetail configurations to provide further stability.

Because of the tight fit required for the operation of this embodiment of the invention, in addition, as shown in FIG. 9*b*, each of the interlocking recesses that form the cooperative surfaces of the plating system would be provided with a snap-in piece (96) that would cover the recess prior to installation of the new plate to ensure that the groove remains unfouled prior to surgery. In addition, although not shown in the figures, an optional window could also be provided in the plate system to allow for the inspection of the disc space.

Although the embodiment shown in FIG. 9 would require the removal and replacement of the vertebral attachment during a revision surgery, it should be understood that the current invention is also directed to external interlocking plate systems in which the vertebral attachment screws of the original plate may be left in place during revision surgery. Exemplary embodiments of such a cervical plating system are shown, for example, in FIGS. 10 to 16, which are discussed in greater detail below.

As shown in FIGS. 10*a* to 10*c*, similar to the embodiment of FIG. 9 that has a partially external gripping portion, the two plates (1000 and 1001) have cooperative recesses (1002 and 1003) which engage each other to form an integrated plate. However, unlike the embodiment shown in FIG. 9*c*, where the interlocked plates would form a common passage through which vertebral attachment screws would pass, in the current embodiment the original plate 10001 has three openings for screws within its interlocking groove 1003. There are two recessed openings 1004 through which vertebral attachment screws 1005 can pass, but it further has a threaded opening 1007 into which a revision plate anchoring screw 1006 would be inserted.

As shown in detail in FIGS. 10*b* and 10*c*, the interlocking groove 1003 of the original plate 1001 is capped with a groove cover 1008 prior to revision. This snap-in cover protects the groove prior to installation of the new plate to ensure that the groove remains unfouled before surgery. Although the caps shown in FIGS. 10 to 16 all only provide protection to the groove itself, it should be understood that the cap could be formed to mimic the externally gripping portion of the revision overlap, thereby providing additional protection to the lateral edge of the pre-positioned plate.

During revision surgery the cap 1008 is removed and the revision plate 1000 is locked into the now exposed cooperating groove. Then the plate anchoring screw 1007 can be inserted through a hole 1009 in the top of the revision plate and into the cooperative threaded opening 1006 on the original plate 1002. Using such a mechanism, allows for the attachment of a revision plate via a single screw, and without the need to disturb the vertebral attachment screws in the original plate.

As seen in FIGS. 10*a* to 10*c*, each revision plate has one end having an interlocking undercut 1002, that allows for the interlocking attachment with the recessed groove 1003 of the original plate, and an opposite end that has a interlocking upper recessed groove 1003' identical to the groove 1003 on the original plate that would allow for additional revision plates to be attached in serial in second, third or fourth level revision surgeries.

Figure 11A:
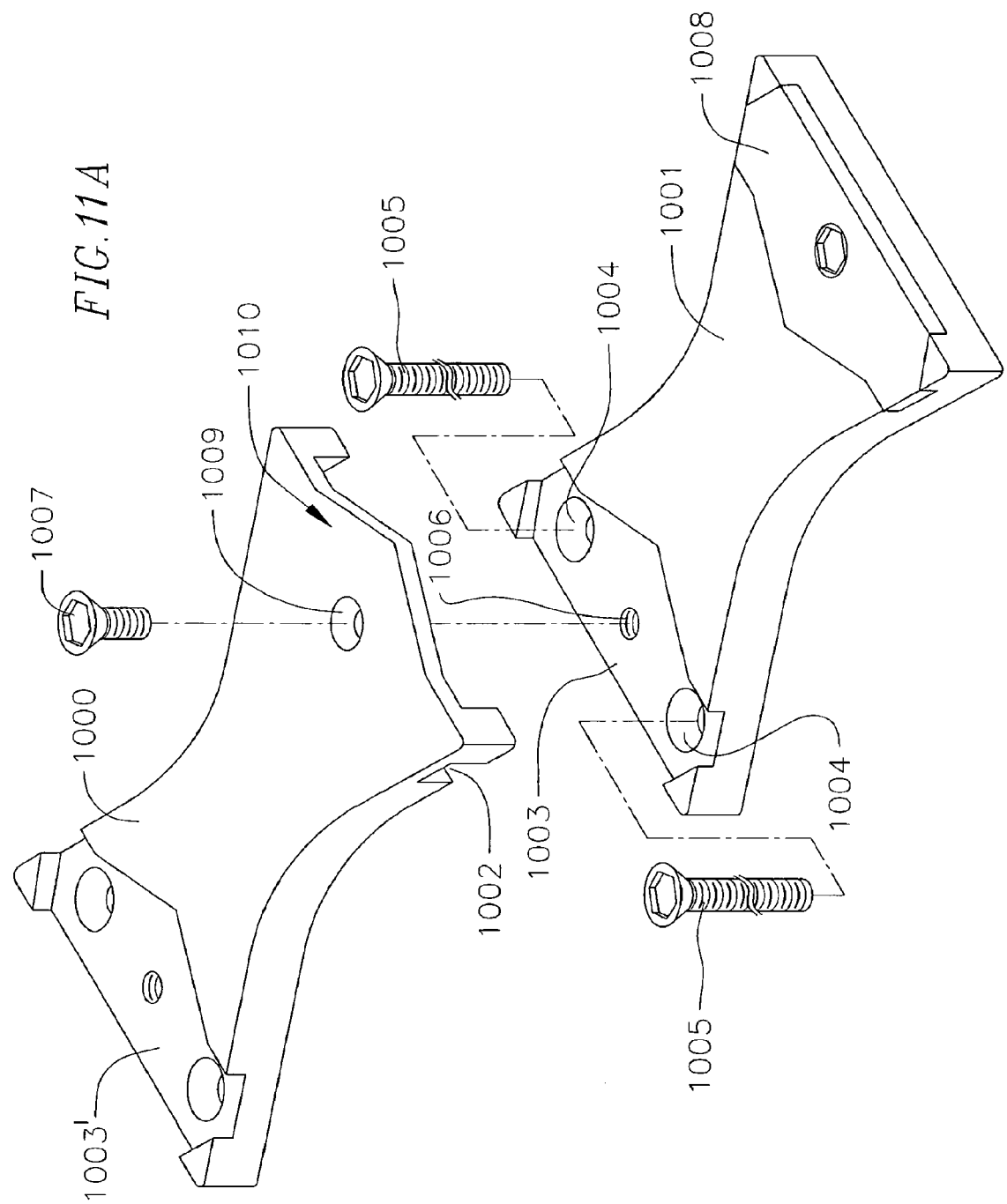
Figure 14E:
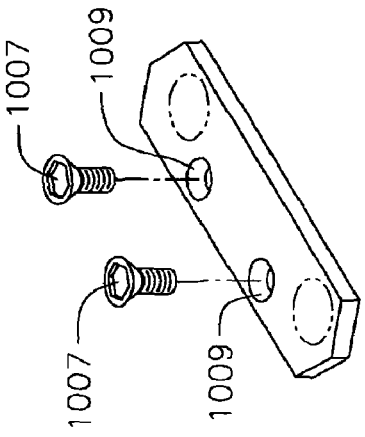
FIGS. 14a to 14f are directed to an alternative embodiment of the embodiment of the anterior cervical plating system in accordance to the current invention provided in FIG. 9.
Figure 14F:
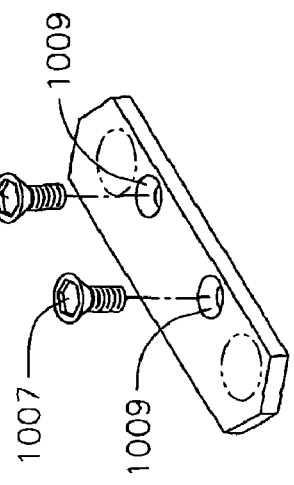
Figure 14C:
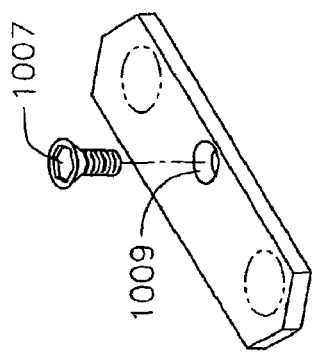
Figure 14D:
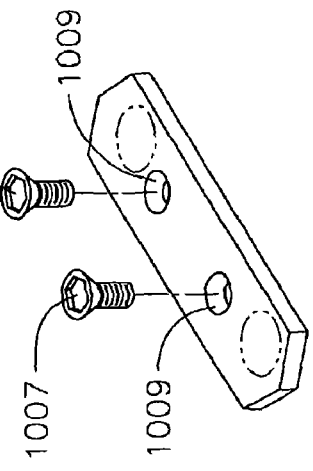
Figure 14A:
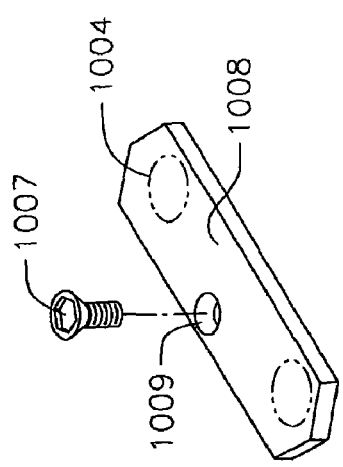
Figure 14B:
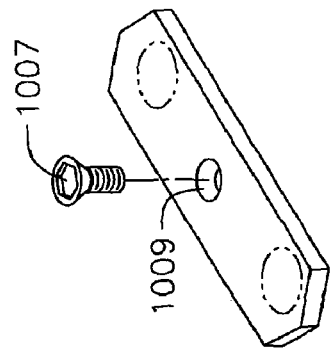

Although only one exemplary groove design has been discussed above, it should be understood that any suitable interlocking groove geometry could be employed in the current embodiment. For example, as shown in FIGS. 11*a* to 11*c*, the groove could include a more complicated interlocking surface, such as a chevron (or triangular section) 1010, or as shown in FIGS. 12*a* to 12*c* a curved surface 1011, to provide additional stability.

One problem that is sometimes experienced during revision surgery occurs when there is an axial misalignment between the longitudinal axis of the original plate and that of the adjacent spine. In such a case, were a revision plate to be simply added in a straight line at the end of the original plate it would be misaligned with the vertebra upon which it is to be anchored. In such cases it would be advantageous to be able to adjust, even slightly, the axis of the adjacent plate. In one alternative embodiment of the external gripping plate shown in FIGS. 9 to 12, the interlocking grooves are designed with tolerances that provide for a small amount of rotation to allow for a radial adjustment of the revision plate. Some exemplary embodiments of such a system are provided in FIGS. 13*a* to 13*g*.

As shown in FIGS. 13*a* and 13*b*, in one very basic form the interlocking groove 1003 of the original plate 1001 is provided with a curve face 1012 that allows for the interlocking face of the revision plate 1013 to rock along its edge allowing for a radial angular adjustment 1014 that serves to provide an adjustment to the longitudinal axis of the revision plate 1000. As shown, this modification does not effect the overall design of the plate or the interlocking mechanism, it merely engineers an angular adjustment mechanism into such a plate.

Although the design in FIGS. 13*a* and 13*b* would provide a minimal amount of angular change, further revisions to the plates could enhance this capability. For example, as shown in FIGS. 13*c* and 13*d*, the interlocking edge 1013 of the revision plate 1001 could be design to cooperate with the curved edge 1012 of the original plate. In such an embodiment, angular displacement of the revision plate could be achieved (as shown in FIG. 13*d*) while providing enhanced interlocking stability between the plates. It should also be understood that although the groove on each of these embodiments is provided with a convex shape, in this interlocking design the curve could also be concave.

In addition, although only simple single hole interconnecting screws have been shown thus far in the radially adjustable plate systems, it should be understood that the extent of angular revision possible could be enhanced by allowing the plate anchoring screw 1007 to move in the revision plate hole 1009, such as by forming a slot 1014, as shown in FIGS. 13*e* and 13*d*, or by including several pre-positioned holes 1015 within which the interlocking plate anchoring screw 1007 may be moved, as shown in FIG. 13*g*.

Finally, although only single interlocking plate anchoring screws 1007 have been shown thus far, it should be understood that any number and disposition of screws may be used to attach the revision plate to the original plate. For example, in FIGS. 14a to 14f a number of possible geometries for single and double interlocking anchoring screw designs are shown. In addition, although each of the embodiments shown in FIGS. 14a to 14g describe interlocking plate anchoring screws that are separate from the vertebral attachment screws 1004, in FIG. 15 another possible embodiment is shown in which the threaded shafts 1006 for the plate anchoring screws 1009 are positioned inside the vertebral attachment screws 1005. In this embodiment it will be understood that special vertebral attachment screws would need to be used in which the threaded connections 1006 are formed into the shaft 1016 of the vertebral attachment screw itself.

Finally, although all of the embodiments of this externally interlocking plate have been shown with the interlocking plate anchoring screws exposed, it should be understood that for extra protection these screws could be covered with a separate snap-in cover 1017, as shown in FIGS. 16a to 16c. Although not necessary, such a snap-in plate may further include a removal tool attachment point 1018, such as a slot for insertion of a flat edge screw driver, that would allow for the easy removal of the cover when the interlocking plate anchor screw needs to be accessed.

Although not shown, all such systems as shown in FIGS. 9 to 16 could also be provided with groove locks on the edges to the plate, such as those discussed in relation to the other dovetail configurations to provide further stability. In addition, although not shown in the figures, an optional window could also be provided in the plate system to allow for the inspection of the disc space.

Although only plating systems having interlocking mechanisms designed around four screw plates have been discussed thus far, it should also be understood that other suitable designs can be contemplated in which the cooperative surfaces interlock around single hole plates. Although a number of different embodiments are provided, the principal feature of the one-hole plating system is that the cooperative faces lock about a single screw hole to anchor one end of the plates to the spine. Using such a one-hole design allows for a low profile stackable add-on plating system.

Turning to the specific embodiments of the one-hole plating system, FIGS. 17a and 17b show an attachment system in which the new plate (90) is attached to the pre-positioned plate (92) via a stackable system in which a interlocking projection (94) on the new plate fits into a cooperative recess (96) of the pre-positioned plate. As shown, once interlocked together, a single screw (98) is positioned through both plates to lock them into place. Although the screw is necessary to attach the plates to the vertebra, the interlocking cooperative surfaces of the two plates provide additional stability by ensuring that the plates cannot slide in relation to one another when screwed into position.

In another configuration of a one-hole plate system, as shown in FIGS. 18a to 18e, has an interlocking arrangement where the new plate (100) snaps around the outside edge of the pre-installed plate (102). In such an embodiment, the coordinating surfaces of the plates may include a recessed arrangement as shown in FIGS. 18a and 18b, where the new plate has a recessed lip (104) upon which a cooperating edge of the pre-installed plate fits, or the pre-installed plate may be supplied with an external groove (106) to engage a cooperative groove (108) disposed on the inner edge of the new plate (100).

Figure 19A:
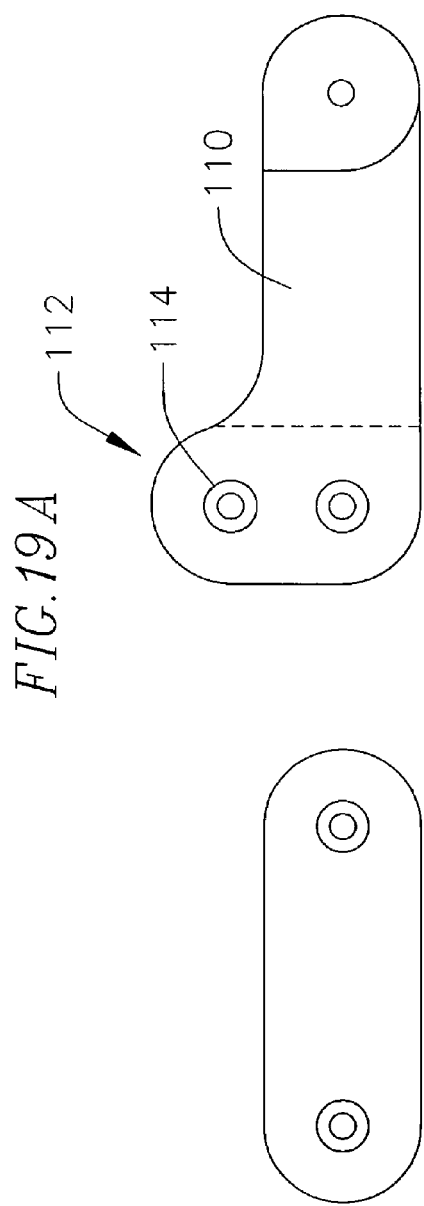
FIGS. 19a and 19b are directed to an twelfth embodiment of an anterior cervical plating system according to the current invention.
Figure 19B:
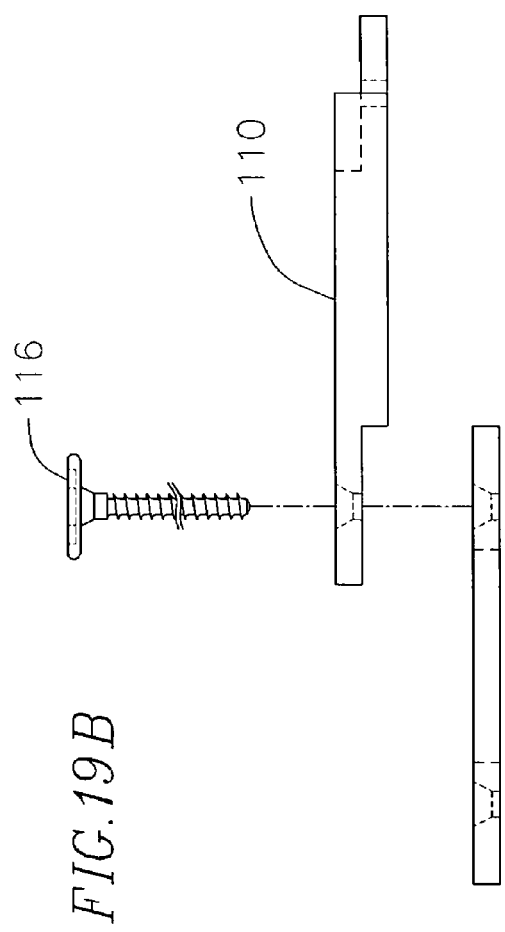

Finally, although the above one-hole plate system designs have all incorporated two identical one-hole plates. It should be understood that the new plate may be provided with additional vertebral securing means to improve the lateral stability of the plate system. For example, in one embodiment shown in FIGS. 19a and 19b, the new revision plate (110) is "L" shaped and the projecting arm (112) is provided with a second screw hole (114) that allows for an additional stabilizing screw (116) to be inserted into the vertebral body. Although a right-handed "L" is shown in the diagram, it should be understood that the projecting arm may be disposed in either direction. Apart from this additional stabilizing screw hole, the plates may interlock using any of the systems described above.

In addition, although not shown in the figures, each of the interlocking recesses and/or grooves that form the cooperative surfaces of the one-hole plating systems described above could be provided with a snap-in piece that would cover the recess/groove prior to installation of the new plate to ensure that the recess/groove remains unfouled prior to surgery. In addition, although not shown in the figures, an optional window could also be provided in the plate system to allow for the inspection of the disc space.

Again, although a few specific embodiments of interlocking/revisable one-hole cervical plating systems are described above, it should be understood that a wide variety of one-hole plating systems may be incorporated with interlocking cooperative surfaces integrated therein such that stable revision of the plates may be undertaken without necessitating the removal of any pre-installed plates.

Although the above embodiments have all included plating systems in which the new plate interlocks within or around the body of the pre-installed plate, it should be understood that any suitable revisable plating system that provides a system of surfaces that cooperate to provide a measure of stability independent from the anchoring screw may be used in the current invention. For example, FIGS. 20 to 22 show various schematics of an embodiment of the invention in which the plates of the plating system are interlocked using a buttress fit. In the buttress fit plating system only the leading edges (117) of the new and old plates interlock, as shown, for example, in FIG. 20c. In such an embodiment, a variety of grooves (FIGS. 20a to 20c, elements 117a and 117b), or tabs (FIG. 21a to 21c, elements 118a and 118b) or interference fits (FIG. 22a to 22c, elements 119a and 119b) could be used to interlock the plates. Such a system would allow the new plate to be added on to the previously placed plate without a more involved system of interlocking portions.

Such buttress fittings could be used as the sole means of interlocking the plates, or they can be used in conjunction with one of the interlocking systems described above. Where such a buttress fit is used as the sole means of interlocking two plates an additional locking cap or tab (120), as shown in FIGS. 21a to 21c) may be included to provide additional stability. Where such a buttress fit is used in conjunction with another interlock system, it can be used as a feature of the other interlocking system, can be an independent feature, or can be an add-on feature, giving yet additional stabilizing support for the plating system.

Figure 23A:
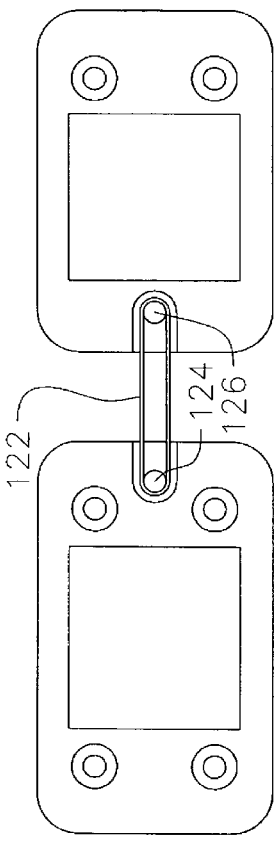
FIGS. 23a and 23b are directed to a sixteenth embodiment of an anterior cervical plating system according to the current invention.
Figure 23B:
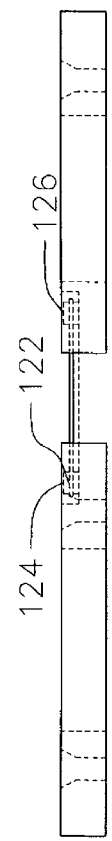
Figure 24A:
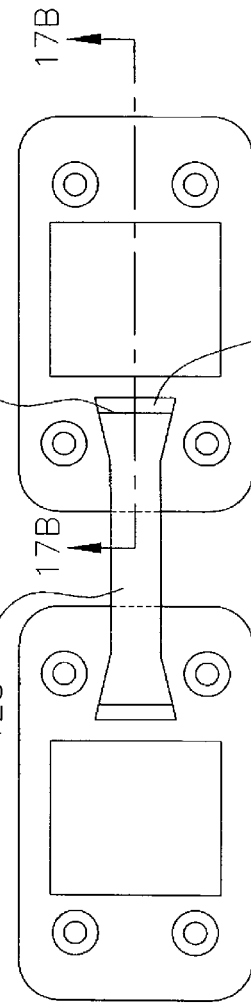
FIGS. 24a and 24b are directed to a seventeenth embodiment of an anterior cervical plating system according to the current invention.
Figure 24B:

Finally, although only systems having metal-on-metal or rigid interlocking portions have been described thus far, it should be further understood that dynamic and flexible interlocking systems are also contemplated by the current invention. For example, FIGS. 23 and 24 provide schematics of exemplary embodiments of plating systems that are interlocked only through flexible bands or strands. As shown in FIGS. 23a and 23b, in the simplest embodiment of such a system, a tension band (122), which could be a metal or even polymer material, such as, for example braided Teflon or Surgistrand, would link two plates by attaching between connectors (124 & 126) on the new plate and pre-installed plate respectively. Alternatively, as shown in FIGS. 24a and 24b, one could also use a metal or polymer connector (128) based on an interlocking system having ends (130) that would cooperate with grooves (132) in the two plates. In either embodiment, an additional locking mechanism, such as, for example, a screw, or a bar/rod with a ratcheting mechanism, could be used to both fixedly attach the band and even tension the band between the two plates if necessary. Although such a flexible band would not be able to provide a rigid stabilizing effect, it would provide a dynamic tension that would stabilize the plate system in all directions under stress.

Although the above discussion have focused on plating systems that operate by linking between the gaps in the vertebral anchors (e.g., the screws) it should be understood that the same system of providing a stable linkage without disturbing the fixation of the pre-positioned plate could be provided by overlapping one or more of the vertebral anchors of the pre-positioned plate. Exemplary embodiments of such systems are shown in FIGS. 25a to 25d.

Figure 25D:
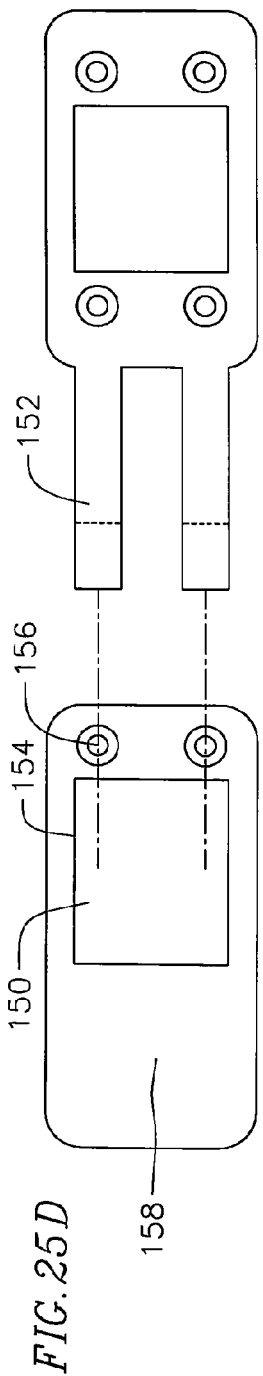
Figure 25E:
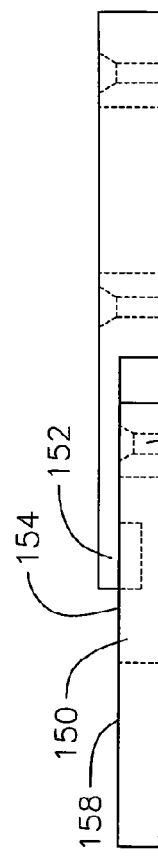
Figure 25F:
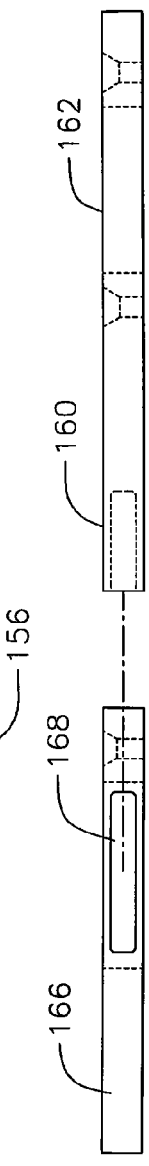
Figure 25G:
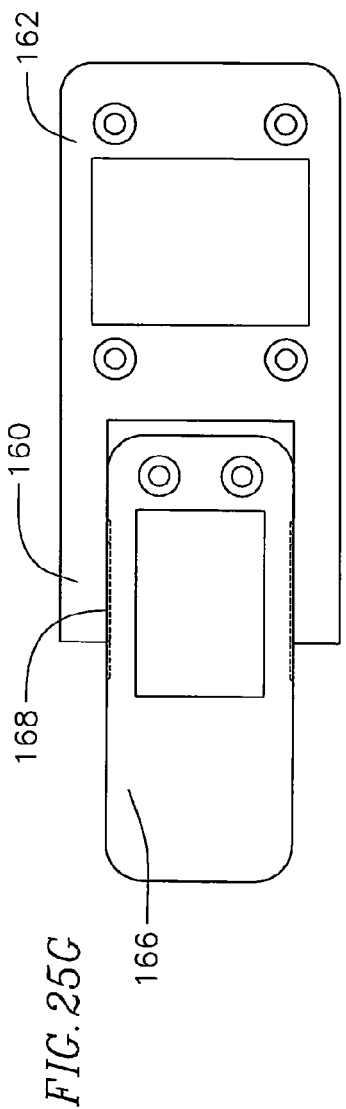

In one exemplary embodiment, as shown in FIGS. 25a to 25c, either the cooperative interlocking device, or armature (140) of the revision plate (142) could be contoured to wrap over the top of the screws (144) of the pre-positioned plate (146) and link with a channel (148) formed in body of the plate either by moving distally (FIG. 25a) or proximally (FIG. 25c) into the channel (25a and 25c), or as shown in FIG. 25b the channel (148) itself could be formed at an elevation higher than the screws (144) allowing the armature (140) to slide into position over the top of the screws. Alternatively, as shown in FIGS. 25d and 25e, in embodiments of plates with windows (150), the armature of the cooperative interlocking mechanism (152) could be designed to engage the edges (154) of the window thereby providing a locking mechanism without requiring a significant spacing between the vertebral anchors (156) on the pre-positioned plate (158). Finally, as shown in FIGS. 25f and 25g, the armatures of the cooperative interlocking mechanism (160) of the revision plate (162) could be formed to engage the outer edges (164) of the pre-positioned plate (166) again providing a stabilizing mechanism without requiring a spacing between the vertebral anchors (168).

It should be understood that while certain channel/armature and groove configurations are provided in the above-discussion, these are only provided as examples, and any of the embodiments of linkage mechanisms provided in this disclosure could be modified to engage over or around the vertebral anchors instead of between them.

Finally, although specific locking mechanism have been discussed in relation to a few of the plating systems described above, it should be understood that any of the plating systems could incorporate a supplementary locking mechanisms to further ensure the stability of the interlock between the pre-installed plate and the new plate. For example, a covering plate that could be incorporate into any of the previously described plating systems could be designed to slide or affixed over the interlocking portions of the plating system thereby preventing a disconnect between the two plates. Likewise an expansion or crimped tab could be provided, which could be engaged over the interlocking portion of the plating system after the plates have been positioned. In yet another embodiment, a rotating plate or bar could be placed overlying the interlocking portion of the plating system. Indeed, it should be understood that these mechanisms are only exemplary, and any suitable mechanism that is capable of locking the interlocking portion of the plating system together may be used in the current invention.

Figure 26A:
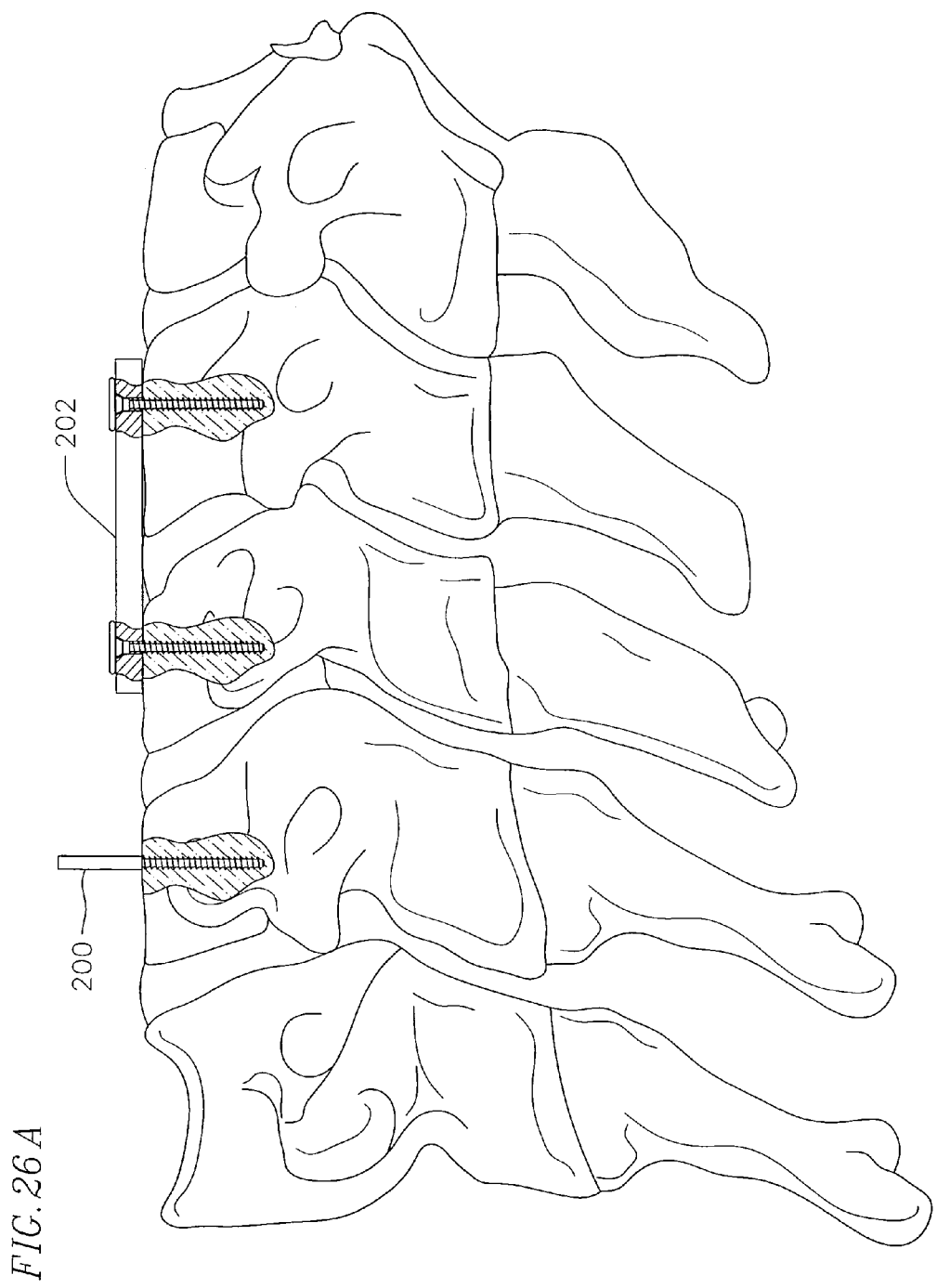
Figure 26B:
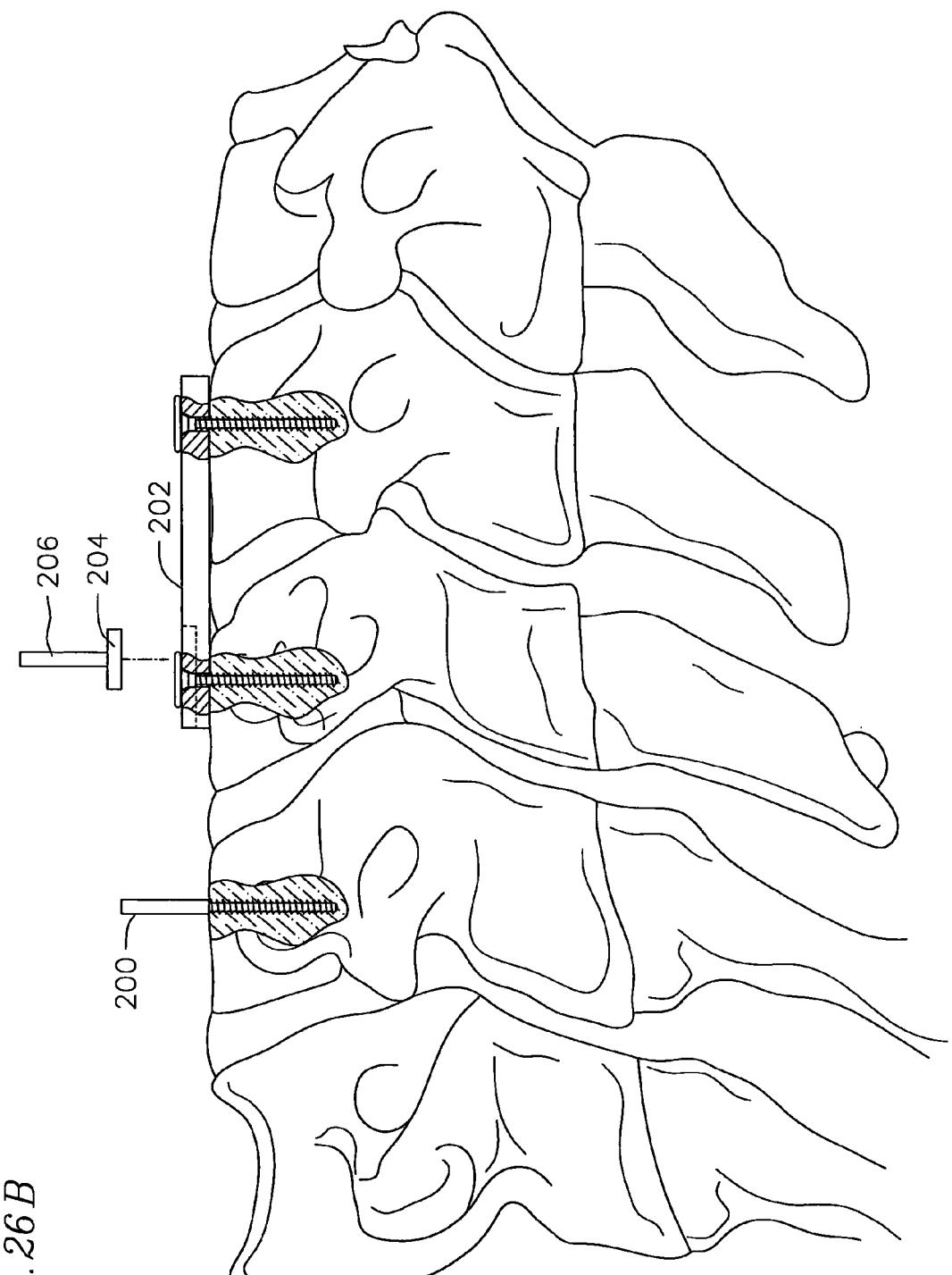

An additional device for use with the new plating system is a distraction system. An exemplary embodiment of a distraction system is provided in FIGS. 26a to 26d. In this embodiment, a distractor could be placed on the pre-installed plate to distract off the plate. The current method of distraction requires the placement of a distraction pin into a vertebra below a disk space, and a second pin placed in the vertebra above a disk space. These are long screws in pins that provide sufficient purchase that a distracter can be placed overlying these pins, and then a distraction force applied between the pins to open the disk space. In the current invention, a single distraction pin (200) would be placed in the vertebra above or below the pre-installed plate (202), and then a mechanism (204) for hooking either a second pin (206) or the distractor (208) itself into the interlock mechanism of the pre-installed plate could be provided so that the plate would not need to be removed. Alternatively, as shown in FIG. 26d, the distractor (208) could be provided with an engaging element (210) that could be directly inserted between the vertebra to provide a stable face to distract the vertebra.

In either embodiment, once in place, this device could be used to distract off the previously placed plate. Alternatively, such a system could be used to place the plate system into compression. Either way, the distractor could be designed as a component of the modular plating system to allow for further revision flexibility without requiring the removal or replacement of the pre-installed plate.

Regardless of the actual design, the features of the current plating system incorporate basic surgeon demands. These include ease of use, few instruments, flexibility, safety, and a sense of security for the surgeon and patient. The additional stacking or modular plates can be incorporated to allow the new plate to settle, incorporating dynamism, or may be applied rigidly. Surgeons can choose these options during the operation, either allowing screws to toggle in the plate, or for the plate to settle relative to the screws.

Although the above discussion has focused on the structure of the anterior cervical plating system of the current invention, it should be understood that the current invention is also directed to surgical methods using such a system. In addition, the system of the current invention can also be used with post-distraction systems, which can be affixed to one vertebra and a plate, or to two plates. These instruments can also be used to compress constructs.

Moreover, although the plates shown in the above figures have been exclusively directed to one level surgeries, it should be understood that the underlying structures are adaptable to two, three, and four level neck surgeries as well. In addition, although only cervical fusions have been discussed, the system of the current invention also has application in a variety of cervical spinal problems, including degenerative conditions, discectomy as well as corpectomy, deformity, trauma, tumor, and infection. Moreover, is further possible to use any of the current cervical plating systems with an artificial disc added to an adjacent level, either as the primary or secondary surgery> in such an embodiment, this adjacent level may be joined by a similar cooperatively interlocking mechanism.

Although specific embodiments and exemplary embodiments are disclosed herein, it is expected that persons skilled in the art can and will design alternative cervical plating systems and methods of using such systems that are within the scope of the following claims either literally or under the Doctrine of Equivalents.

What is claimed is:

1. An anterior cervical plating system comprising:
a plurality of cervical plates, each plate being defined by longitudinal and latitudinal axes and bone facing and top surfaces, the boundaries of said surfaces being defined by a pair of lateral surfaces and proximal and distal surfaces, wherein the lateral surfaces face outward from the centerline of the longitudinal axis and are disposed between the distal and proximal surfaces, and wherein the distal and proximal surfaces are disposed at the ends of the plates and face outward from the centerline of the latitudinal axis, said plates further having at least a first vertebral anchoring means and each further having at least two interlocking portions;

each of the interlocking portions having at least two armatures, said interlocking portions being designed to engage and interlock an interlocking portion on an adjacent cervical plate to provide a stabilizing interconnection therebetween, the stabilizing interconnection being capable of resisting movement of the cervical plates in at least one dimension;

wherein both of the interlocked interlocking portions of each pair of interlocked plates engage one of either the distal or proximal outward facing surface of the adjacent interlocked plate, and wherein the at least two armatures of each of said interlocking portions engage at least a portion of both of the outward facing lateral surfaces of the adjacent interlocked plate to form the stabilizing interconnection; and wherein the stabilizing interconnection is fixed into place via at least one anchoring connector that is inserted through at least one cooperative channel formed between the interconnected cooperative interlocking portions, and where the operation of said at least one anchoring connector is independent of any of the vertebral anchoring means of the system.

2. The system of claim 1, comprising at least one pre-positioned cervical plate and at least one revision cervical plate;
wherein the pre-positioned cervical plate is interconnected with the adjacent revision cervical plate via the stabilizing interconnection.

3. The system of claim 2, wherein at least one of the interlocking portions on the pre-positioned cervical plate comprises a groove integrally formed into the top portion of one of either the distal or proximal ends of the pre-positioned cervical plate, and at least one of the interlocking portions of the revision cervical plate comprises an undercut interlockingly cooperative with said groove, the undercut being integrally formed on at least one of either the distal or proximal ends of the revision-cervical plate.

4. The system of claim 3, wherein the groove and undercut are interlocking mirror images.

5. The system of claim 3, wherein the groove and undercut are formed into a cooperative shape selected from the group consisting of rectangular, triangular or curved.

6. The system of claim 3, wherein the vertebral anchoring means comprises at least one vertebral screw.

7. The system of claim 6, wherein the at least one vertebral screw is positioned within a recessed hole disposed in the grooves of each of the plates.

8. The system of claim 7, wherein the undercut of the adjacent plate is in one of at least the distal or proximal ends of the cervical plate and engages with the groove such that the undercut overlaps said at least one vertebral screw when interlocked with the groove.

9. The system of claim 3, wherein the at least one anchoring connector is at least one screw, and the at least one cooperative channel is a threaded channel defined by the undercut and the groove, into which the at least one screw is engaged to prevent movement between the adjacent plates.

10. The system of claim 9, wherein the anchoring connector is a single screw.

11. The system of claim 9, wherein the anchoring connector is a pair of screws.

12. The system of claim 9, wherein at least a portion of the at least one threaded channel is formed into the top of the at least one vertebral screw.

13. The system of claim 9, wherein each of the at least one threaded channels further comprises a removable anchoring connector cap for protectively covering the entire upper surface of the anchoring connector.

14. The system of claim 1, wherein each of the cervical plates further comprises a removable interlocking portion cap for protectively covering the entirety of the interlocking portion of the cervical plate when said base interlocking portion is unengaged with a corresponding cooperative interlocking portion, and wherein said removable cap is lockingly engaged to said plate by said anchoring connector.

15. The system of claim 14, wherein each of the removable interlocking portion caps further comprises a separate removable anchoring connector cap for protectively covering the entire upper surface of the anchoring connector.

16. The system of claim 14, wherein each of the removable interlocking portion caps further includes an external gripping portion disposed to protect the portions of the outward facing lateral surfaces of the plate where the cooperative interlocking portion will be engaged.

17. The system of claim 3, wherein at least the inner edge of the groove defines a radial curve such that the revision plate may be radially adjusted such that a new longitudinal axis is defined between the pre-positioned plate and the revision plate.

18. The system of claim 17, wherein the inner edge of the undercut is formed to cooperate with the radical curve of the groove.

19. The system of claim 18, wherein the radial curve is one of either concave or convex.

20. The system of claim 17, wherein the anchoring connector is at least one screw, and the undercut and the groove further define at least one cooperative threaded channel into which the at least one screw is engaged to prevent movement between the adjacent plates, and wherein at least the undercut portion of the threaded channel is formed as a slot.

21. The system of claim 20, wherein at least the undercut portion of the threaded channel has a plurality of pre-set angularly displaced positions through which said anchor screw may be threaded.

22. The system of claim 1 wherein each of the cervical plates further comprise an opening formed in the body of the plate disposed such that said opening overlaps and allows visual inspection of the disc space between two adjacent vertebra when said cervical plate is anchored in position.

23. The system of claim 2, wherein the system further comprises at least a second revision cervical plate interconnected at the end of the pre-positioned cervical plate opposite the first revision cervical plate through a second interlocking portion of the second revision cervical plate and a second interlocking portion of the pre-positioned plate.

24. The system of claim 2, wherein at least a second revision cervical plate is interconnected to the end of the first revision cervical plate opposite the pre-positioned cervical plate through an interlocking portion of the first revision cervical plate and an interlocking portion of the second revision cervical plate.

25. A method of performing an anterior cervical fusion utilizing the anterior cervical plating system comprising:
providing a patient with at least one previously installed bone plate;

providing at least one additional cooperative revision bone plate wherein both the previously installed and additional cooperative revision bone plates comprise the following:

said plates being defined by longitudinal and latitudinal axes and bone facing and top surfaces, the boundaries of said surfaces being defined by a pair of lateral surface and distal surfaces, wherein the lateral surfaces face outward from the centerline of the longitudinal axis and are disposed between the distal and proximal surfaces, and wherein the distal and proximal surfaces are disposed at the ends of the plates and face outward from the centerline of the latitudinal axis, said plates further having at least a first vertebral anchoring means and further having at least two interlocking portions, each of the interlocking portions of each of said plates having at least two armatures, said interlocking portions being designed to engage and interlock an interlocking portion on an adjacent cervical plate to provide a stabilizing interconnection therebetween, the stabilizing interconnection being capable of resisting movement of the cervical plates in at least one dimension, wherein the interlocking portions of the plates are designed to engage one of either the distal or proximal outward facing surface of the adjacent interlocked plate, and wherein the at least two armatures of each of said interlocking portions engage at least a portion of both of the outward facing lateral surfaces of the adjacent interlocked plate to form the stabilizing interconnection, and wherein the stabilizing interconnection is designed to be fixed into place via at least one anchoring connector that is inserted through at least one cooperative channel formed between the interconnected cooperative interlocking portions, and where the operation of said at least one anchoring connector is independent of any of the vertebral anchoring means of the system; and joining the previously installed bone plate to the revision bone plate by interconnecting the interlocking portions of the plates and fixing said interlocking portions into place via the at least one anchoring connector.

26. A method of performing an anterior cervical fusion revision comprising:

providing a patient with at least one previously installed bone plate;

providing at least one additional cooperative revision bone plate wherein both the previously installed and additional cooperative revision bone plates comprise the following:

an elongated body defined by longitudinal and latitudinal axes and bone facing and top surfaces, the boundaries of said surfaces being defined by a pair of lateral surfaces and proximal and distal surfaces, wherein the lateral surfaces face outward from the centerline of the longitudinal axis and are disposed between the distal and proximal surfaces, and wherein the distal and proximal surfaces are disposed at the ends of the plates and face outward from the centerline of the latitudinal axis;

at least one plate interlock disposed on the elongated body, said at least one plate interlock being designed to engage and cooperatively interconnect the elongated body to a cooperative plate interlock disposed on an adjacent plate by engaging one of either the distal or proximal outward facing surface of the adjacent interlocked plate, and at least a portion of both of the outward facing lateral surfaces of the adjacent interlocked plate, at least one bone anchor having a bone engaging portion at one end and a drive portion at the other, said at least one bone anchor being arranged in relation to the elongated body such that said at least one bone anchor can affix the elongated body to a bone, wherein the cooperative plate interlocks are fixed into place via at least one anchoring connector that is inserted through at least one cooperative channel formed between the plate interlocks, and where the operation of said at least one anchoring connector is independent of the at least one bone anchor of the revisable bone plate, and at least one removable cap, each of said at least one removable caps being designed to engage with and cover the entirety of one of the at least one plate interlocks and the portion of the outward facing lateral surfaces of said plate adjacent said interlock to prevent the fouling of the interlock and outward facing lateral surfaces of the plate adjacent to said interlock when said interlock is unengaged with the adjacent plate;

removing the at least one removable caps from interlocking portions to be used to join the plates; and joining the previously installed bone plate to the revision bone plate by interconnecting the interlocking portions of the plates and fixing said interlocking portions into place via the at least one anchoring connector.

27. A revisable bone plate comprising:

an elongated body defined by longitudinal and latitudinal axes and bone facing and top surfaces, the boundaries of said surfaces being defined by a pair of lateral surfaces and proximal and distal surfaces, wherein the lateral surfaces face outward from the centerline of the longitudinal axis and are disposed between the distal and proximal surfaces, and wherein the distal and proximal surfaces are disposed at the ends of the plates and face outward from the centerline of the latitudinal axis;

at least one plate interlock disposed on the elongated body, said at least one plate interlock being designed to engage and cooperatively interconnect the elongated body to a cooperative plate interlock disposed on an adjacent plate by engaging one of either the distal or proximal outward facing surface of the adjacent interlocked plate, and at least a portion of both of the outward facing lateral surfaces of the adjacent interlocked plate;

at least one bone anchor having a bone engaging portion at one end and a drive portion at the other, said at least one bone anchor being arranged in relation to the elongated body such that said at least one bone anchor can affix the elongated body to a bone;

wherein the cooperative plate interlocks are fixed into place via at least one anchoring connector that is inserted through at least one cooperative channel formed between the plate interlocks, and where the operation of said at least one anchoring connector is independent of the at least one bone anchor of the revisable bone plate; and at least one removable cap, each of said at least one removable caps being designed to engage with and cover the entirety of one of the at least one plate interlocks and the portion of the outward facing lateral surfaces of said plate adjacent said interlock to prevent the fouling of the interlock and outward facing lateral surfaces of the plate adjacent to said interlock when said interlock is unengaged with the adjacent plate.

28. The revisable bone plate of claim 27, further comprising:
    at least one opening formed in the elongated body such that said at least one opening overlaps and allows visual inspection of the portion of the body beneath the plate when said plate is anchored in position; and
    at least one removable insert, each of said at least one removable inserts being designed to engage with and cover the entirety of one of the at least one openings to prevent the fouling of the opening when not in use.

29. The revisable bone plate of claim 27, wherein the at least one removable cap is held in place by mechanism selected from the group consisting of screws, bolts, o-rings and snap-fittings.

30. The revisable bone plate of claim 28, wherein the at least one removable insert is held in place by mechanism selected from the group consisting of screws, bolts, o-rings and snap-fittings.

31. The revisable bone plate of claim 27, wherein the at least one removable cap is held in place by a threaded connector; and wherein the cap further comprises a separate removable portion designed to cover the entirety of the upper surface of said threaded connector.

32. The revisable bone plate of claim 28, wherein the at least one removable insert is held in place by a threaded connector; and wherein the insert further comprises a separate removable portion designed to cover the entirety of the upper surface of said threaded connector.

33. The revisable bone plate of claim 27, further comprising:
    at least one removable bone anchor cover designed to cover the entirety of the drive portion of the at least one bone anchor.

34. The revisable bone plate of claim 33, wherein the at least one removable bone anchor cover and the at least one removable cap are a single integrated piece.

* * * * *